(12) United States Patent
Sedelmeier et al.

(10) Patent No.: US 8,143,416 B2
(45) Date of Patent: Mar. 27, 2012

(54) ALTERNATIVE SYNTHESIS OF RENIN INHIBITORS AND INTERMEDIATES THEREOF

(75) Inventors: Gottfried Sedelmeier, Schallstadt (DE); Stuart John Mickel, Lausen (CH); Heinrich Rueeger, Flueh (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/022,243

(22) Filed: Feb. 7, 2011

(65) Prior Publication Data
US 2011/0137044 A1 Jun. 9, 2011

Related U.S. Application Data

(62) Division of application No. 11/573,790, filed as application No. PCT/EP2005/009347 on Aug. 30, 2005, now Pat. No. 7,910,774.

(30) Foreign Application Priority Data

Aug. 31, 2004 (GB) .................................. 0419361.1

(51) Int. Cl.
*C07D 263/52* (2006.01)
(52) U.S. Cl. ....................................................... 548/224
(58) Field of Classification Search .................... 548/224
See application file for complete search history.

(56) References Cited

U.S. PATENT DOCUMENTS 5,936,116 A  8/1999  Martin et al.

FOREIGN PATENT DOCUMENTS

| EP | 0 678 503 | 9/1999 |
| EP | 1 215 201 | 10/2006 |
| WO | 03/103653 | 12/2003 |

OTHER PUBLICATIONS

Beard et al, Tetrahedron, vol. 52, No. 10, pp. 3719-3740, 1996.*
Goschke et al. (2003) "The nonchiral bislactim diethoxy ether as a highly stero-inducing sython for sterically hindered, γ-branched α-amino acids: a practical, large-scale route to an intermediate of the novel renin inhibitor aliskiren"; Helvetica Chimica Acta, 86: 2824-2870.
Hanessian et al. (2002) "The power of visual imagery in synthesis planning, stereocontrolled approaches to CGP-60536B, a protein renin inhibitor"; J. Org. Chem, 67: 4261-4274.
Rueger et al. (2000) "A convergent synthesis approach towards CGP60536B, a non-peptide orally potent rennin inhibitor, via an enantiomerically pure ketolactone intermediate"; Tetrahedron Letters, 41: 10085-10089.
Sandham et al. (2000) "A convergent synthesis of the renin inhibitor CGP60536B"; Tetrahedron Letters, 41: 10091-10094.

* cited by examiner

*Primary Examiner* — Shailendra Kumar
(74) *Attorney, Agent, or Firm* — Ann R. Pokalsky, Esq.; Dilworth & Barrese, LLP

(57) ABSTRACT

The present invention relates to synthetic routes to prepare a compound of the formula

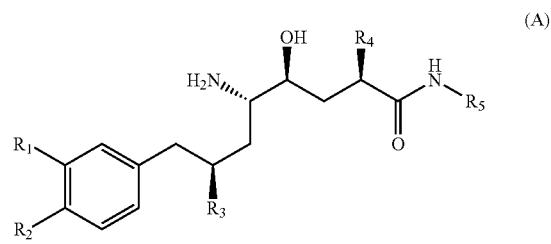

(A)

wherein $R_1$ is halogen, $C_{1-6}$halogenalkyl, $C_{1-6}$alkoxy-$C_{1-6}$alkyloxy or $C_{1-6}$alkoxy-$C_{1-6}$alkyl; $R_2$ is halogen, $C_{1-4}$alkyl or $C_{1-4}$alkoxy; $R_3$ and $R_4$ are independently branched $C_{3-6}$alkyl; and $R_5$ is cycloalkyl, $C_{1-6}$alkyl, $C_{1-6}$hydroxyalkyl, $C_{1-6}$alkoxy-$C_{1-6}$alkyl, $C_{1-6}$alkanoyloxy-$C_{1-6}$alkyl, $C_{1-6}$aminoalkyl, $C_{1-6}$alkylamino-$C_{1-6}$alkyl, $C_{1-6}$dialkylamino-$C_{1-6}$alkyl, $C_{1-6}$alkanoylamino-$C_{1-6}$alkyl, HO(O)C—$C_{1-6}$alkyl, $C_{1-6}$alkyl-O—(O)C—$C_{1-6}$alkyl, $H_2$N—C(O)—$C_{1-6}$alkyl, $C_{1-6}$alkyl-HN—C(O)—$C_{1-6}$alkyl or $(C_{1-6}$alkyl$)_2$N—C(O)—$C_{1-6}$alkyl; or a pharmaceutically acceptable salt thereof as well as key intermediates obtained when following these routes as well as their preparation.

6 Claims, No Drawings

ALTERNATIVE SYNTHESIS OF RENIN INHIBITORS AND INTERMEDIATES THEREOF

This application is a divisional application of U.S. application Ser. No. 11/573,790, filed Mar. 29, 2007, now U.S. Pat. No. 7,910,774 which is a 371 application of PCT/EP05/09347, filed August 30, 2005.

The present invention provides methods for preparing certain 2(S),4(S),5(S),7(S)-2,7-dialkyl-4-hydroxy-5-amino-8-aryl-octanoyl amide derivatives, or pharmaceutically acceptable salts thereof. The present invention further relates to novel intermediates useful in the manufacture of the same.

More specifically, the 2(S),4(S),5(S),7(S)-2,7-dialkyl-4-hydroxy-5-amino-8-aryl-octanoyl amide derivatives to which the methods of the present invention applies are any of those having renin inhibitory activity and, therefore, pharmaceutical utility, e.g., those disclosed in U.S. Pat. No. 5,559,111.

Surprisingly, it has now been found that 2(S),4(S),5(S),7(S)-2,7-dialkyl-4-hydroxy-5-amino-8-aryl-octanoyl amide derivatives are obtainable in high diastereomeric and enantiomeric purity using pyro-glutamic acid, in particular, L-pyro-glutamic acid, as the starting material.

In particular, the present invention provides a method for the preparation of a compound of the formula

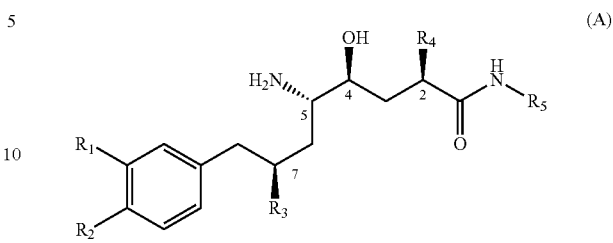

wherein $R_1$ is halogen, $C_{1-6}$halogenalkyl, $C_{1-6}$alkoxy-$C_{1-6}$alkyloxy or $C_{1-6}$alkoxy-$C_{1-6}$alkyl; $R_2$ is halogen, $C_{1-4}$alkyl or $C_{1-4}$alkoxy; $R_3$ and $R_4$ are independently branched $C_{3-6}$alkyl; and $R_5$ is cycloalkyl, $C_{1-6}$alkyl, $C_{1-6}$hydroxyalkyl, $C_{1-6}$alkoxy-$C_{1-6}$alkyl, $C_{1-6}$alkanoyloxy-$C_{1-6}$alkyl, $C_{1-6}$aminoalkyl, $C_{1-6}$alkylamino-$C_{1-6}$alkyl, $C_{1-6}$dialkylamino-$C_{1-6}$alkyl, $C_{1-6}$alkanoylamino-$C_{1-6}$alkyl, $HO(O)C$—$C_{1-6}$alkyl, $C_{1-6}$alkyl-O—(O)C—$C_{1-6}$alkyl, $H_2N$—C(O)—$C_{1-6}$alkyl, $C_{1-6}$alkyl-HN—C(O)—$C_{1-6}$alkyl or $(C_{1-6}$alkyl$)_2$N—C(O)—$C_{1-6}$alkyl; or a pharmaceutically acceptable salt thereof; which method comprises starting from L-pyro-glutamic acid and following reaction steps as outlined in Scheme 1a.

Scheme 1a: A method for preparing a compound of formula (A) starting from N— and O— protected 5-hydroxymethyl-3-substituted isopropyl pyrrolidinone (IV).

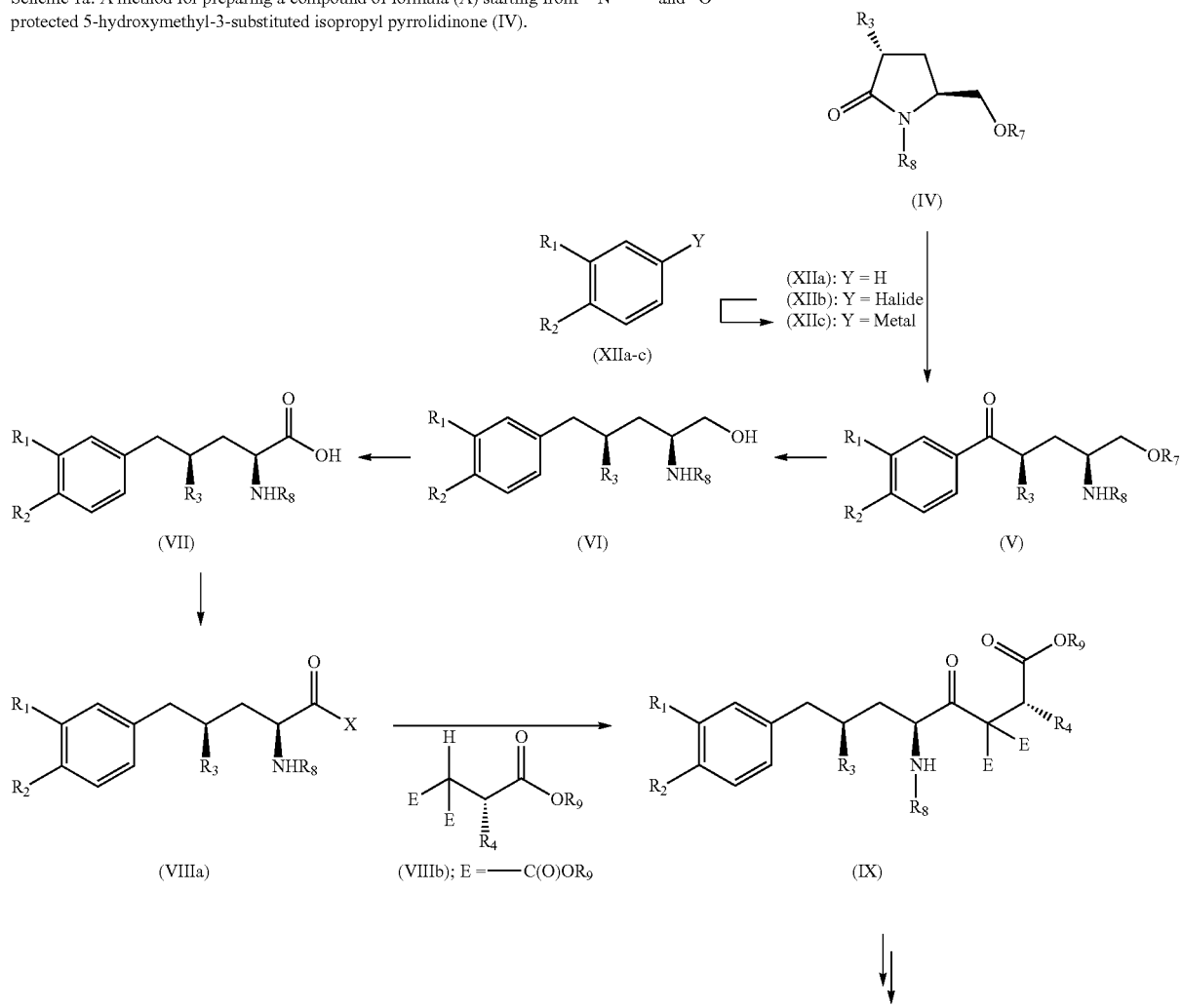

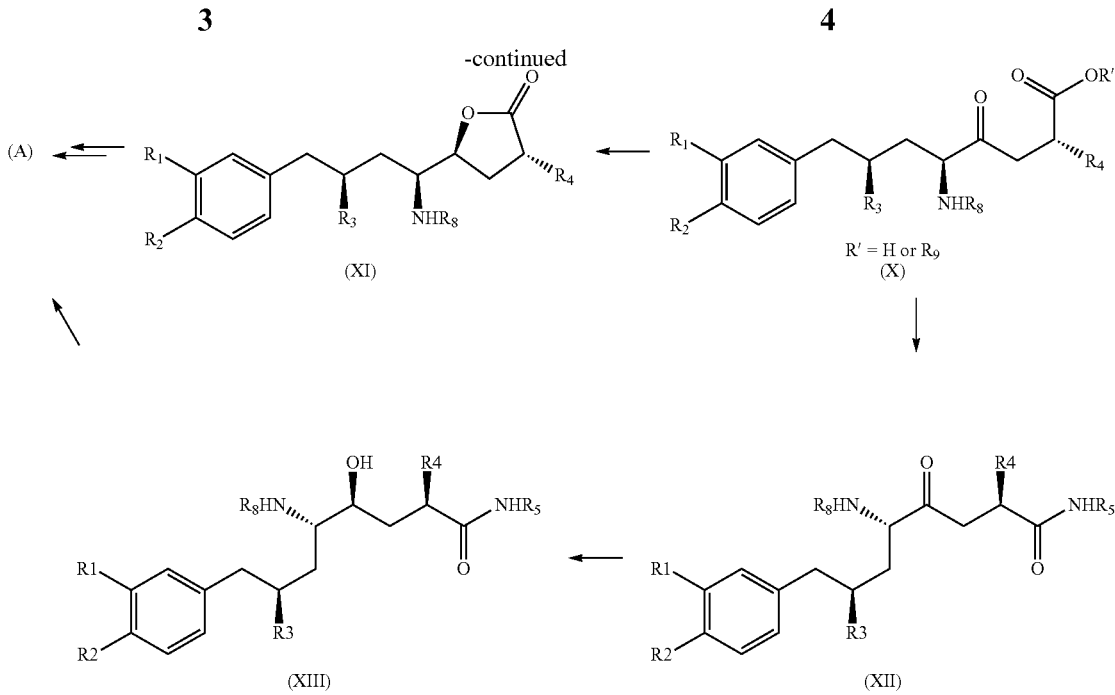

Compound (IV) can be prepared from from L-pyro-glutamic acid via the unprotected 5-hydroxymethyl-3-substituted isopropyl pyrrolidinone (III) as shown in the first steps of Schemes 1b and 1.

Thus, the present invention provides also a method for the preparation of a compound of the formula (A)

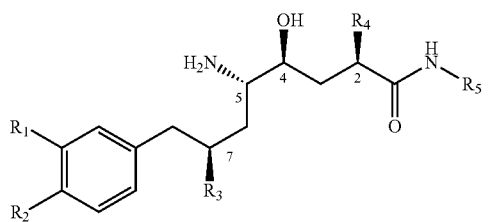

wherein $R_1$ is halogen, $C_{1-6}$halogenalkyl, $C_{1-6}$alkoxy-$C_{1-6}$alkyloxy or $C_{1-6}$alkoxy-$C_{1-6}$alkyl; $R_2$ is halogen, $C_{1-4}$alkyl or $C_{1-4}$alkoxy; $R_3$ and $R_4$ are independently branched $C_{3-6}$alkyl; and $R_5$ is cycloalkyl, $C_{1-6}$alkyl, $C_{1-6}$hydroxyalkyl, $C_{1-6}$alkoxy-$C_{1-6}$alkyl, $C_{1-6}$alkanoyloxy-$C_{1-6}$alkyl, $C_{1-6}$aminoalkyl, $C_{1-6}$alkylamino-$C_{1-6}$alkyl, $C_{1-6}$dialkylamino-$C_{1-6}$alkyl, $C_{1-6}$alkanoylamino-$C_{1-6}$alkyl, HO(O)C—$C_{1-6}$alkyl, $C_{1-6}$alkyl-O—(O)C—$C_{1-6}$alkyl, $H_2N$—C(O)—$C_{1-6}$alkyl, $C_{1-6}$alkyl-HN—C(O)—$C_{1-6}$alkyl or $(C_{1-6}$alkyl$)_2$N—C(O)—$C_{1-6}$alkyl; or a pharmaceutically acceptable salt thereof; which method comprises starting from L-pyro-glutamic acid and following reaction steps as outlined in Scheme 1b.

Scheme 1b: A method for preparing a compound of formula (A) starting from L-pyro-glutamic acid.

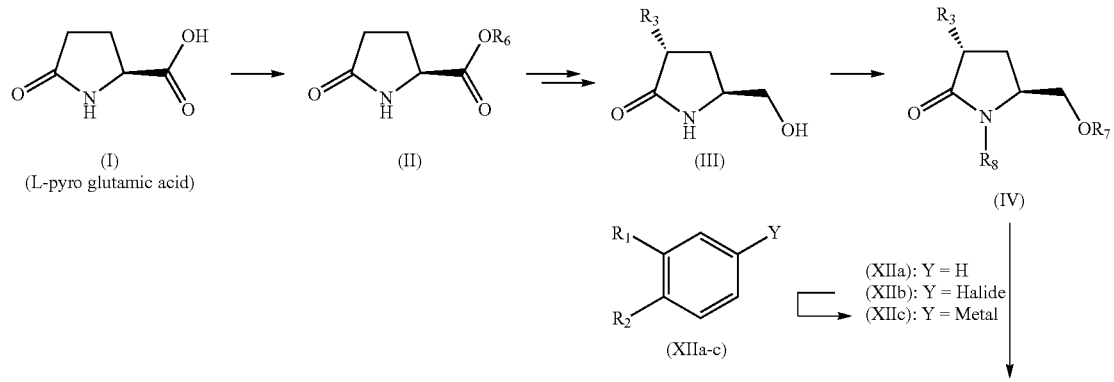

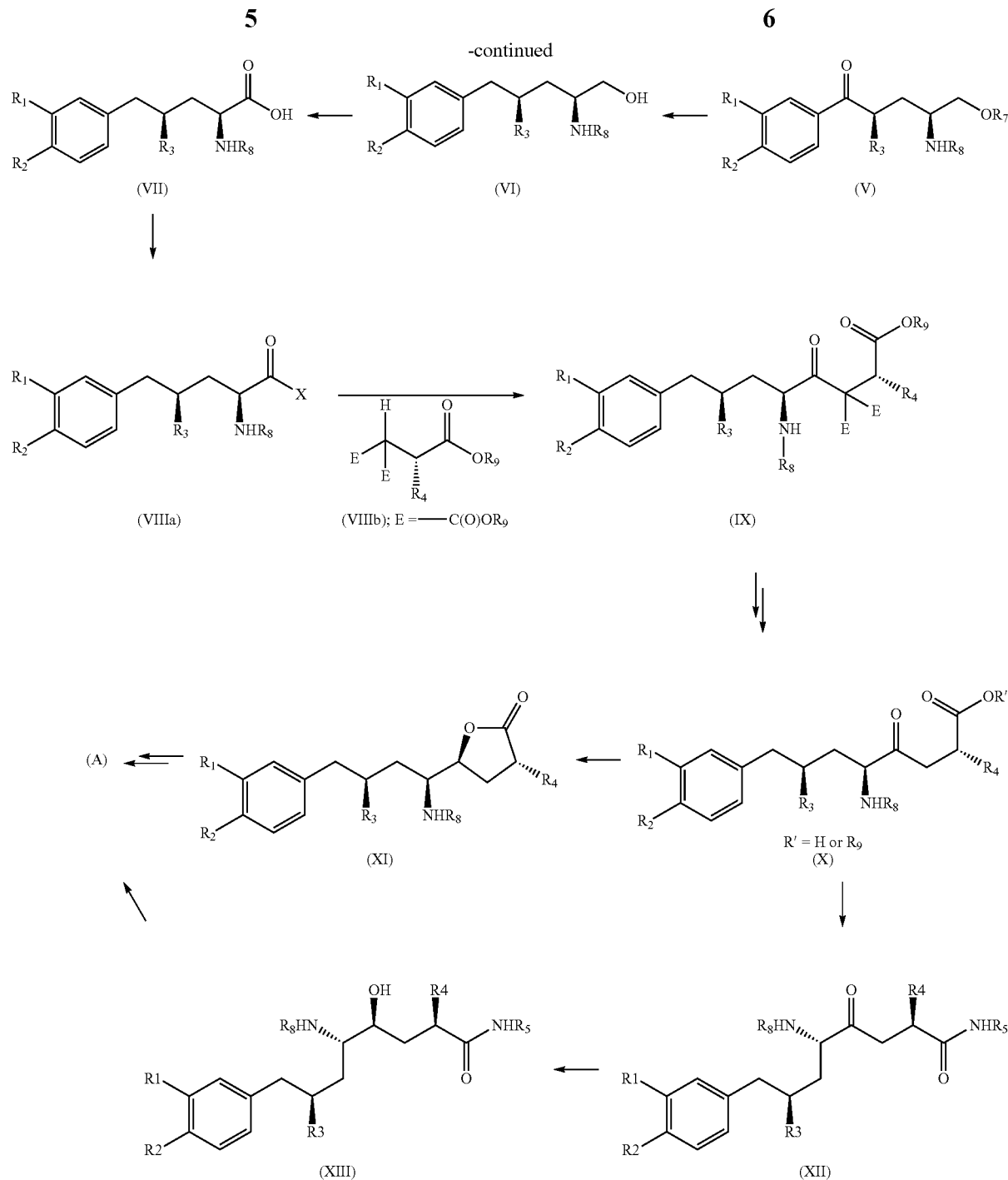

The present invention provides also a method for the preparation of a compound of the formula

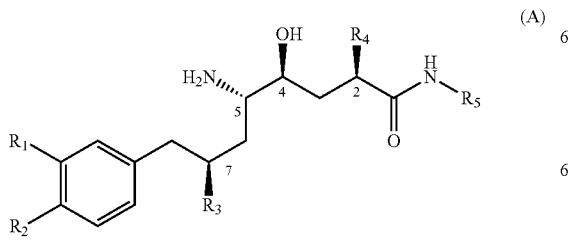

wherein $R_1$ is halogen, $C_{1-6}$halogenalkyl, $C_{1-6}$alkoxy-$C_{1-6}$alkyloxy or $C_{1-6}$alkoxy-$C_{1-6}$alkyl; $R_2$ is halogen, $C_{1-4}$alkyl or $C_{1-4}$alkoxy; $R_3$ and $R_4$ are independently branched $C_{3-6}$alkyl; and $R_5$ is cycloalkyl, $C_{1-6}$alkyl, $C_{1-6}$hydroxyalkyl, $C_{1-6}$alkoxy-$C_{1-6}$alkyl, $C_{1-6}$alkanoyloxy-$C_{1-6}$alkyl, $C_{1-6}$aminoalkyl, $C_{1-6}$alkylamino-$C_{1-6}$alkyl, $C_{1-6}$dialkylamino-$C_{1-6}$alkyl, $C_{1-6}$alkanoylamino-$C_{1-6}$alkyl, HO(O)C—$C_{1-6}$alkyl, $C_{1-6}$alkyl-O—(O)C—$C_{1-6}$alkyl, $H_2N$—C(O)—$C_{1-6}$alkyl, $C_{1-6}$alkyl-HN—C(O)—$C_{1-6}$alkyl or $(C_{1-6}alkyl)_2N$—C(O)—$C_{1-6}$alkyl; or a pharmaceutically acceptable salt thereof; which method comprises starting from L-pyro-glutamic acid and following reaction steps as outlined in Scheme 1.

Scheme 1: A method for preparing a compound of formula (A) starting from L-pyro-glutamic acid.

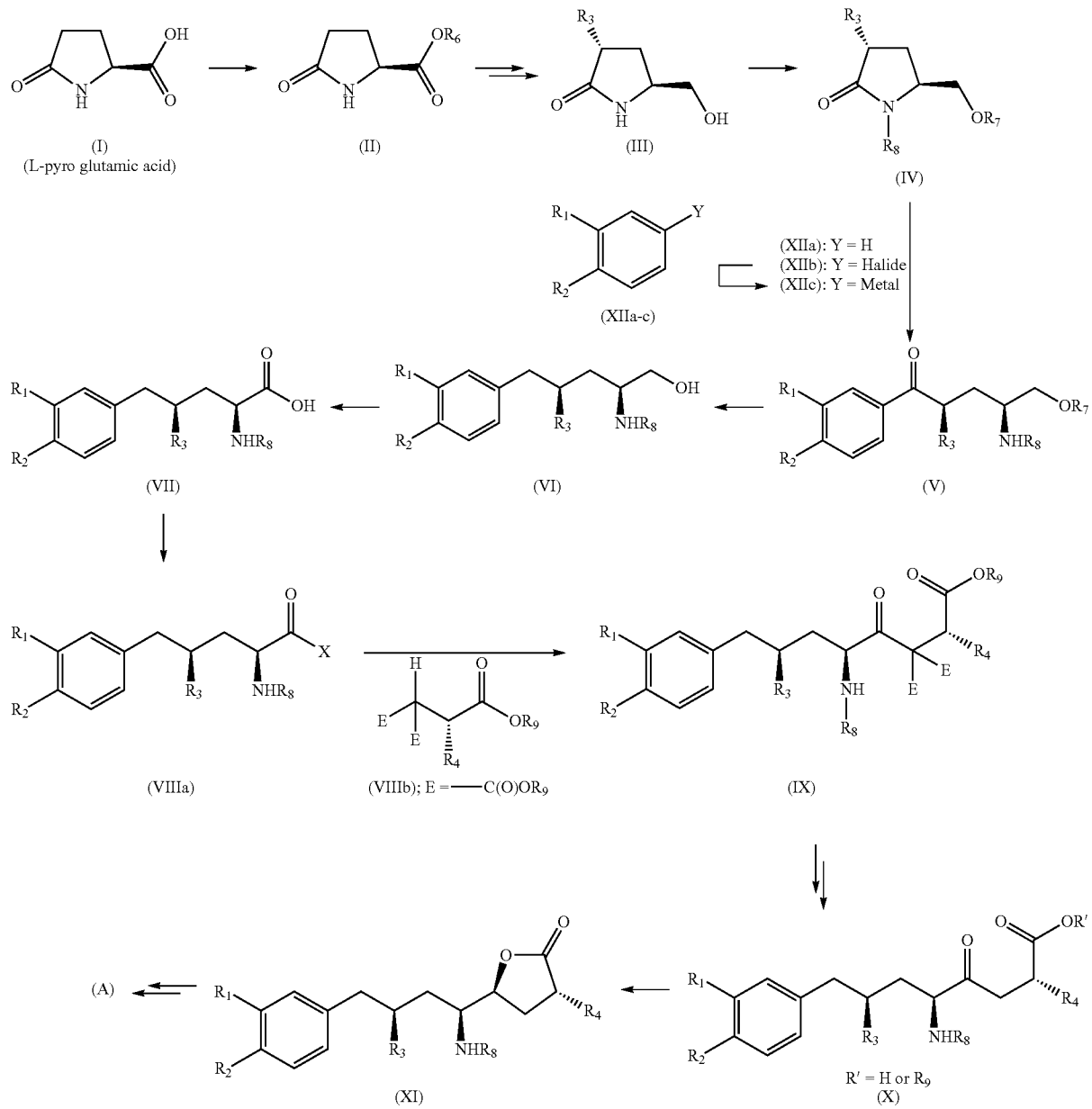

In each of the schemes the variants have the same meaning as set forth for the compounds of formula (A) or as explained below.

Compounds of formula (III), wherein $R_3$ has meaning as defined for formula (A), are key intermediates in the methods of the present invention having the desired stereochemistry already at place at carbons corresponding to position 5 and 7 in the compounds of formula (A).

As illustrated in Schemes 1b and 1, compounds of formula (III) wherein $R_3$ has meaning as defined herein above, may be obtained starting by esterification of L-pyro-glutamic acid according to methods illustrated herein in the Examples, or using methods well known in the art, to afford compounds of formula (II) wherein $R_6$ is $C_{1-20}$alkyl, $C_{3-12}$cycloalkyl, $C_{3-12}$cycloalkyl-$C_{1-6}$alkyl, $C_{6-10}$aryl or $C_{6-10}$aryl-$C_{1-6}$alkyl, more preferably $C_{1-6}$alkyl, still more preferably $C_{1-4}$alkyl, most preferably methyl or ethyl. Compounds of formula (II) may then be converted to compounds of formula (III) following the reaction steps as exemplified below in Scheme 2.

Scheme 2: Conversion of a compound of formula (II) to a compound of formula (III).

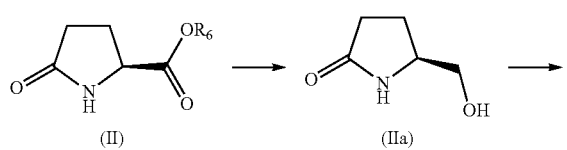

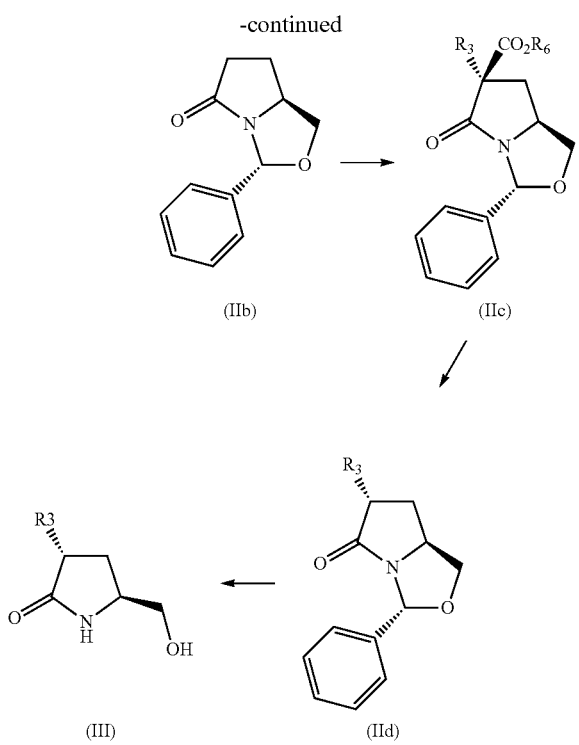

(IIb)   (IIc)

(III)   (IId)

a) According to Scheme 2 Compound (II), wherein $R_6$ has meanings as defined herein, is reduced to afford the corresponding alcohol (IIa). The reduction is typically conducted with a complex borohydride like $LiBH_4$ or $NaBH_4$ in the presence of LiCl in an appropriate solvent like THF, etc. a mixture of THF and an alcohol as for example EtOH, i-PrOH, etc. to compound (IIa) as known from literature. Reference is made to 1a) M. Moloney et al., Tetrahedron, 52, (10) 3719 (1996)

b) Compound (IIa) is acetalized with an aromatic aldehyde to yield compound of formula (IIb), wherein the phenyl ring shown in the structure may be substituted by one or more, e.g. two or three, residues e.g. those selected from the group consisting of $C_1$-$C_7$-alkyl, hydroxy, $C_1$-$C_7$-alkoxy, $C_2$-$C_8$-alkanoyl-oxy, halogen, nitro, cyano, and $CF_3$. Acetalization of compound of formula (IIa) is preferably performed with benzaldehyde or another aromatic aldehyde according to literature procedures to compound (IIb). Reference is made to 2a) M. Moloney et al., Tetrahedron: Asymmetry, 6, 337 (1995); 2b) M. Moloney et al., Tetrahedron, 52, (10) 3719 (1996).

c) Compound (IIb) is activated by a carboalkoxylation followed by alkylation with an electrophile $R_3$—X, wherein X is a leaving group, e. g. halogen or sulfonyloxy and $R_3$ is as defined hererin, to obtain compound of formula (IIc), wherein the phenyl ring shown in the structure may be substituted by one or more, e.g. two or three, residues e.g. those selected from the group consisting of $C_1$-$C_7$-alkyl, hydroxy, $C_1$-$C_7$-alkoxy, $C_2$-$C_8$-alkanoyl-oxy, halogen, nitro, cyano, and $CF_3$. Preferably, activation proceeds via a carboalkoxylation, e.g. a carbomethoxylation or carboethoxylation, mediated by treatment of (IIb) with e.g. NaH in THF or mixture of THF/DMF followed by a electrophile like a carbonate or a phosgene derivative like Cl—CO—$OR_6$. $R_6$ is as defined herein, preferably $C_{1-6}$alkyl, more preferably $C_{1-4}$alkyl, most preferably methyl or ethyl. This intermediate is then deprotonated and afterwards alkylated with an electrophile like $R_3$—X, wherein $R_3$ is as defined herein, as described in e.g. M. Moloney et al., Tetrahedron, 52, (10) 3719 (1996) to obtain compound (IIc), Especially alkylating such carboalkoxy activated intermediates with branched, secondary alkylating agents like R—C—X—R' is preferred. Leaving groups X can be halogen, sulfonyloxy, etc.

d) Compounds (IIc) are saponified at the ester group followed by decarboxylation to yield compound of formula (IId), wherein the phenyl ring shown in the structure may be substituted by one or more, e.g. two or three, residues e.g. those selected from the group consisting of $C_1$-$C_7$-alkyl, hydroxy, $C_1$-$C_7$-alkoxy, $C_2$-$C_8$-alkanoyl-oxy, halogen, nitro, cyano, and $CF_3$, and $R_3$ is as defined herein. Saponification of compound of formula (IIc) proceeds preferably with aqueous base (NaOH) at the ester group, and then it is acidified and decarboxylated to compounds (IId), which can be distilled in some cases. Reference is made to the literature methods of 2b), above.

e) Compounds (IId) are deacetalised or transacetalised to yield compound of formula (III), wherein and $R_3$ is as defined herein. Deacetalization or transacetalization preferably proceeds by treatment with anhydrous acid like $CF_3COOH$, HCl in toluene or dioxane, or by acid catalysed transacetalisation in the presence of an alcohol to give compounds (III). Reference is made to the literature methods of 2b) above.

Compounds of formula (III) wherein $R_3$ has meaning as defined herein above, may then be converted to compounds of formula (IV) wherein $R_7$ is O-protecting group such as $C_{1-6}$alkyl, $C_{1-6}$alkoxy-$C_{1-6}$alkyloxy, $C_{6-10}$aryl-$C_{1-6}$alkyl, $C_{1-6}$alkoxy-carbonyl, $C_{6-10}$aryl-$C_{1-6}$alkoxycarbonyl or ($C_{1-8}$alkyl)$_3$silyl; and $R_8$ is N-protecting group such as $C_{6-10}$aryl-$C_{1-6}$alkyl, $C_{1-6}$alkyl-carbonyl, $C_{6-10}$aryl-carbonyl, $C_{1-6}$alkoxy-carbonyl, $C_{6-10}$aryl-$C_{1-6}$alkoxycarbonyl; by simultaneous or sequential protection of the hydroxyl and the amino group depending on the nature of $R_7$ and $R_8$. This is typically performed using standard protecting group chemistry following the procedures as described in the literature referenced below.

As an alternative to the first steps outlined in Scheme 1, the compound of formula (IV) can be prepared from the compound of formula (I) shown in Scheme 1 via the route outlined in Scheme 1c.

Scheme 1c: A method for preparing a compound of formula (IV) starting from L-pyro-glutamic acid.

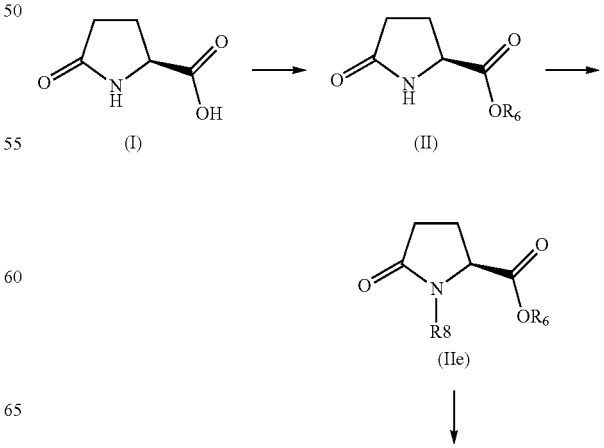

(I)   (II)

(IIe)

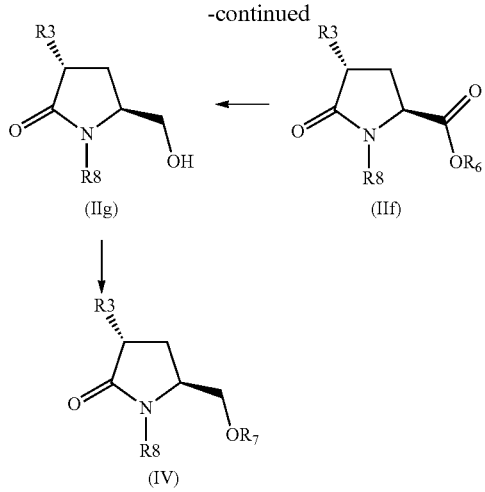

The esterification of the compound of formula (I) typically proceeds according to methods illustrated herein in the Examples, or using methods well known in the art, to afford compounds of formula (II) wherein $R_6$ is as defined above. Compounds of formula (II) are then N-protected to afford compounds of formula (IIe) wherein $R_8$ is an N-protecting group as described above. This is typically performed using standard protecting group chemistry following the procedures as described in the literature referenced below.

As the next step, the compound (IIe) is converted to compound (IIf) according to methods illustrated herein in the Examples, or using methods well known in the art. Accordingly, generation of the anion at position 4 of the pyroglutamic acid ester ring by treatment of IIe with a strong base, e.g. a strong lithium base followed by quenching with acetone in the presence of a Lewis acid provides an intermediate tertiary alcohol. The alcohol group is then converted into a leaving group by reaction with an appropriate electrophile. Elimination then provides the desired compound IIf, wherein $R_3$, $R_6$ and $R_8$ are as defined above. Reference is made to the method described by Hanessian S. et al, J. Org. Chem. 2002, 67, 4261.

Then, the compound (IIf) is converted to compound (IIg) wherein $R_3$ and $R_8$ are as defined above by reducing the ester moiety to the alcohol according to methods illustrated herein in the Examples, or using methods well known in the art, typically by using a hydride such as lithium borohydride.

Compounds of formula (IIg) are then O-protected to afford compounds of formula (IV) wherein $R_7$ is an O-protecting group as described above and $R_3$ and $R_8$ are as defined above, according to methods illustrated herein in the Examples, or using methods well known in the art. This is typically performed using standard protecting group chemistry following the procedures as described in the literature referenced below.

Once compounds of formula (IV) are prepared, preferably by one of the above routes, they are further converted to compounds of formula (V). Reaction with an organometallic compound of formula (XIIc) wherein $R_1$ and $R_2$ have meanings as defined for formula (A); and Y is, e.g. lithium; or (XIIc) represents a Grignard reagent; then affords compounds of formula (V) wherein $R_1$, $R_2$, $R_3$, $R_7$ and $R_8$ have meanings as defined herein above, also key intermediates for the preparation of compounds of formula (A) This is typically performed as illustrated herein in the Examples, or using methods well known in the art, Reference is made to the method described by Houben-Weyl: Volume 4/1c, page 379-386, Reduktion I. Reduction of the benzylic carbonyl group using conventional methods, e.g. those described in "Organikum, organisch-chemisches Grundpraktikum", 20th revised edition, VEB Deutscher Verlag der Wissenschaften, Berlin 1999, followed by selective removal of the O-protecting group affords compounds of formula (VI) wherein $R_1$, $R_2$, $R_3$ and $R_8$ have meanings as defined herein above. This is typically performed as illustrated herein in the Examples, or using methods well known in the art, see e.g. Th. W. Greene & P. G. M. Wuts, "Protective groups in Organic Synthesis", $2^{nd}$ Ed. (1991). See also Raney-Nickel-benzylic deoxygenation: Applied Catalysis A: General 219, page 281-289 (2001).

Compounds of formula (VI) may then be oxidized to carboxylic acids of formula (VII) wherein $R_1$, $R_2$, $R_3$ and $R_8$ have meanings as defined herein above, according to methods illustrated herein in the Examples, or using methods well known in the art, e.g., by treatment with sodium hypochlorite and TEMPO in the presence of a phase transfer catalyst such as $Bu_4NBr$. Reference is made to the methods described by a) F. Montanari et al., J.O.C., 54, 2970 (1989) and b) Review: H. van Bekkum et al., Synthesis 1153 (1996).

Carboxylic acids of formula (VII) may first be converted to their activated derivatives of formula (VIIIa) wherein $R_1$, $R_2$, $R_3$ and $R_8$ have meanings as defined herein above; and X represent e.g. halogen such as fluorine or chlorine; $R_{10}OC(O)O$— in which $R_{10}$ is $C_{1-20}$alkyl, $C_{3-12}$cycloalkyl, $C_{3-12}$cycloalkyl-$C_{1-6}$alkyl, $C_{6-10}$aryl or $C_{6-10}$aryl-$C_{1-6}$alkyl; Me(MeO)N—; or imidazolyl, also key intermediates for the preparation of compounds of formula (A). This is typically performed as illustrated herein in the Examples, or using methods well known in the art, see e.g. for A) acid chlorides, see references a) R. W. Saalfrank et al., Angew. Chem., 102, 292 (1990) & H. Boehme et al., Chem. Ber. 99, 879 (1966) b) Chem. Pharm. Bull., 13, 1472 (1965) & Synth. Commun., 30, 3439 (2000) & Bull. Korean Chem. Soc., Vol. 24, 895 (2003); B) acid fluorides, see reference Tetrahedron Lett., 32, (10) 1303 (1991) C) via imidazolide: see references R. V. Hoffman et al., J.O.C., 62, 2292 (1997) or R. V. Hoffman et al., J.O.C., 62, 6240 (1997) or R. V. Hoffman et al., J.O.C., 67, 1045 (2002), or R. V. Hoffman et al., Tetrahedron, 53, 7119 (1997); or see J. Maibaum & D. Rich, J.O.C., 53, 869 (1988).

Subsequent coupling with a chiral malonate derivative of formula (VIIIb) wherein $R_4$ is as defined for formula (A); and $R_9$ is $C_{1-20}$alkyl, $C_{3-12}$cycloalkyl, $C_{3-12}$cycloalkyl-$C_{1-6}$alkyl, $C_{6-10}$aryl, $C_{2-20}$alkenyl or $C_{6-10}$aryl-$C_{1-6}$alkyl, preferably $C_{1-6}$alkyl or $C_{6-10}$aryl-$C_{1-4}$alkyl, more preferably $C_{1-4}$ alkyl or benzyl, most preferably methyl, ethyl, t-butyl or benzyl; then affords compounds of formula (IX) wherein $R_1$, $R_2$, $R_3$, $R_4$, $R_8$ and $R_9$ have meanings as defined herein above. This is typically performed as illustrated herein in the Examples, or using methods well known in the art, see e.g. Journ. Med. Chem., 41, 2461 (1998).

Ester cleavage and decarboxylation of compound (IX) is conducted to afford compound of formula (X) wherein $R_1$, $R_2$, $R_3$, $R_4$, $R_8$ and $R_9$ have meanings as defined herein above, also key intermediates for the preparation of compounds of formula (A). The ester cleavage is typically a hydrolysis or a hydrogenation, in case of a benzylic ester, according to methods well known in the art. The decarboxylation is typically performed as illustrated herein in the Examples, or using methods well known in the art, see e.g. J. Med. Chem., 41, 2461 (1998). The ester, i.e. the compound of formula (X) wherein R' is $R_9$, can be used as it is for the next step or it can be hydrolysed to the respective acid where R' is H, if desired, prior to the next step. Hydrolysis can be effected according to methods well known in the art.

As the next step the compound of formula (X) is subjected to stereoselective reduction of the C-4 carbonyl group and cyclization upon treatment with acid, which then affords compounds of formula (XI) wherein $R_1$, $R_2$, $R_3$, $R_4$ and $R_8$ have meanings as defined herein above. The stereoselective reduction is typically performed as illustrated herein in the Examples, or using methods well known in the art, Reference is made to e.g. R. V. Hoffman et al. JOC, 67, 1045 (2002) and literature references cited therein and R. V. Hoffman et al., JOC, 62, 2292 (1997), and T. Ikariya et al., J.O.C., 69, 7391 (2004) and literature references cited therein.

The chiral malonate derivative of formula (VIIIb) wherein $R^4$ and $R^9$ are as defined herein which is used in the conversion of compound (VIIIa) as discussed above is an important synthesis building block for the preparation of renin inhibitors. The chiral malonate derivative of formula (VIIIb) is available from a number of sources, eg. D-valine when $R^4$ is isopropyl as shown in Scheme 3 below. In this case $R^9$ is preferably methyl or ethyl. This route is applicable to any branched $C_{3-6}$alkyl for $R^4$.

Scheme 3: Synthesis of compound (VIII'b) wherein $R^4$ is isopropyl using D-valine as the starting material:

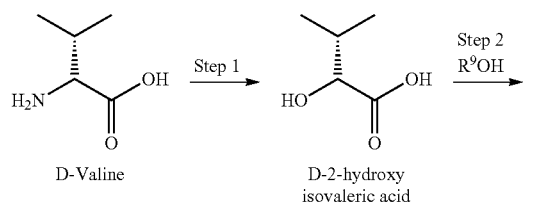

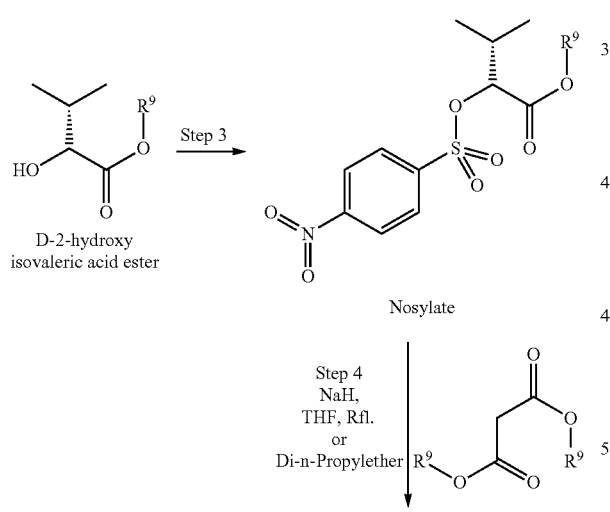

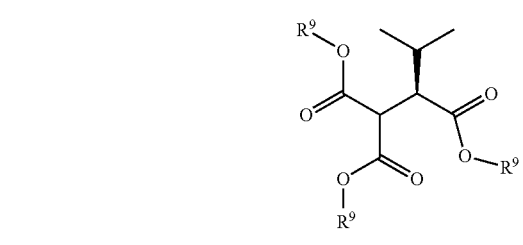

D-valine is converted into D-2-hydroxy isovaleric acid via diazotization using Na nitrite in aqueous sulphuric acid. Alternatively, D-2-hydroxy isovaleric acid can be purchased commercially e.g. from Fluka or Aldrich. According to literature procedures (Tetrahedron, 46, 6623 (1990), J. Chem. Soc.; Perk. Trans. 1, (12), 1427 (1996), J. Org. Chem., 52, 4978 (1987)) the acid is esterified using e.g. potassium carbonate and $R_9$—X, e.g. MeI. As a next step the hydroxyl group of the D-2-hydroxy isovaleric acid ester is esterified with 4-nitrobenzene sulfonyl chloride. This reaction is preferably conducted in the presence of triethylamine and a catalytic amount of DMAP(dimethylaminopyridine) obtaining the R-enantiomer. The sulfonic acid ester or nosylate is then alkylated with a suitable diester, e.g. malonic acid ester under conversion of the stereochemistry to yield the final triester.

Alternatively to the above schemes, compounds of formula (XI) can be obtained via an a route starting from compounds of formula (VI) or (VII), whereby compounds of formula (VI) or (VII) have been obtained by any of the conversions described e.g. in Schemes 1, 1a, 1b, 1c or 2 alone or in combination. This route is outlined in Scheme 4 below. In this Scheme $R_4$ has been shown exemplary as i-propyl in order to better visualize the conversions. However, Scheme 4 is not limited to $R_4$ being i-propyl but the compounds shown can be any branched $C_{3-6}$alkyl as set forth herein. Moreover, although Scheme 4 only illustrates the route using the alcohol (VI) to obtain in the next step the respective aldehyde (XIV), in this alternative route one may also employ the acid (VII) and prepare the respective aldehyde (XIV) via esterification of the acid and subsequent reduction of the ester using DIBAL-H to yield the aldehyde (XIV).

Scheme 4: Alternative approach to prepare compounds of formula (XI) from the alcohol (VI):

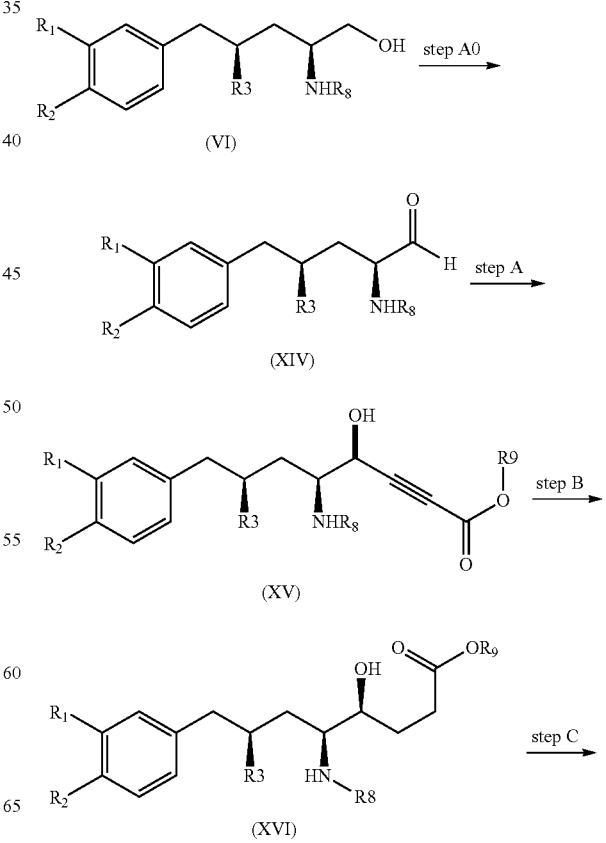

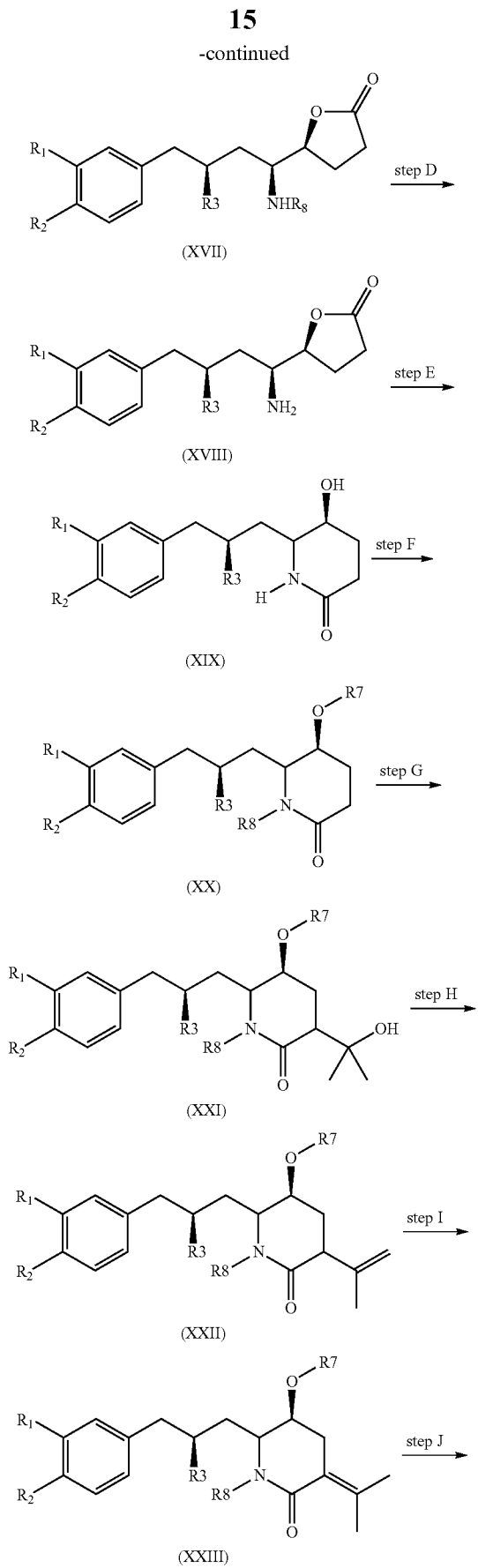
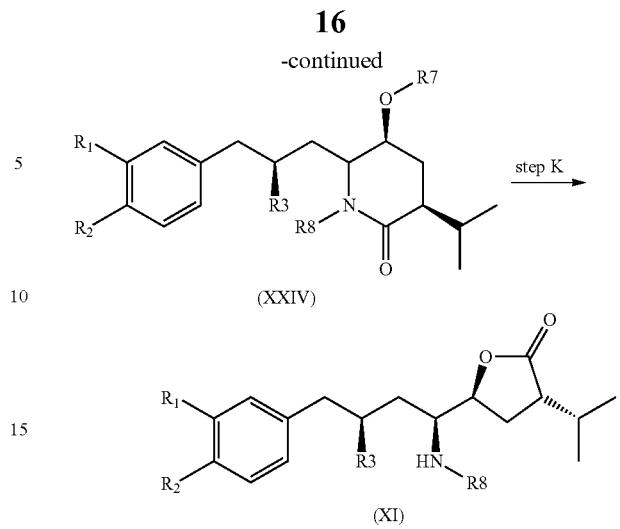

The steps as outlined in Scheme 4 will be described in detail below as well as in the Examples.

Step A0: The N-Boc-protected alcohol (VI) is selectively oxidized to the corresponding aldehyde (XIV) wherein $R_1$, $R_2$, $R_3$, and $R_8$ have meanings as defined herein. Typically this is performed by treatment with bleach and catalytic amounts of Tempo. Preferably, the reaction is conducted under extensive stirring preferably in a biphasic solvent system like water-toluene or water-toluene/EtOAc. Reference is made e.g. to a) F. Montanari et al., J.O.C., 54, 2970 (1989) and b) Review: H. van Bekkum et al., Synthesis 1153 (1996).

Step A: A suitable nucleophile, e.g. a propiolester-Li-salt, is added to the Boc-protected aldehyde (XIV) to yield the acetylenic amino alcohol of formula (XV) wherein $R_1$, $R_2$, $R_3$, $R_8$ and $R_9$ have meanings as defined herein. The reaction is typically performed in THF at −78° C. The resulting acetylenic amino alcohol (XV) is typically obtained as a mixture of diastereomers (S,S) and (S,R). The acetylenic amino alcohol (XV) can be used without separation as the 2 epimers.

Step B: The triple bond of the acetylenic amino alcohol (XV) is hydrogenated to give the saturated γ-hydroxy ester (XVI) wherein $R_1$, $R_2$, $R_3$, $R_8$ and $R_9$ have meanings as defined herein. This conversion is typically performed in a mixture of toluene and acetic acid over platinum oxide. The saturated γ-hydroxy ester (XVI) can be used without further purification.

Step C: The saturated γ-hydroxy ester (XVI) is subjected to lactonization to obtain the γ-lactone of formula (XVII) wherein $R_1$, $R_2$, $R_3$, and $R_8$ have meanings as defined herein. Preferably, this step is performed by treatment with acid, eg. AcOH, preferably in a solvent at elevated temperatures of 50 to 150° C., e.g. in hot toluene for 2 hours at 95-100° C.

Step D: The γ-lactone of formula (XVII) is deprotected on the nitrogen to yield the amino lactone of formula (XVIII) wherein $R_1$, $R_2$ and $R_3$ have meanings as defined herein. This step is preferably performed by treatment with an anhydrous acid, e.g. hydrogen chloride gas in ethyl acetate preferably at room temperature to get the unprotected δ-amino-γ-lactone as e.g. the hydrochloride.

Step E: The amino lactone of formula (XVIII) is converted into the corresponding piperidinone of formula (XIX)) wherein $R_1$, $R_2$ and $R_3$ have meanings as defined herein. This step is preferably performed by treatment in a solvent such as methanol at e.g. room temperature for e.g. 24 hours in the presence of a base. The base can be an amine base, e.g. triethylamine and is preferably used in excess to give the corresponding piperidone.

Step F: The hydroxyl and the amine moieties of the piperidinone of formula (XIX) are protected with a suitable protecting group by procedures well known in the art to give the bis-protected piperidinone of formula (XX) wherein $R_1$, $R_2$, $R_3$, $R_7$ and $R_8$ have meanings as defined herein. Preferably the piperidone from step E is treated in a solvent such as THF with a suitable base, e.g. an amine base such as triethylamine, and a catalyst, e.g. N,N-dimethyl-aminopyridine and a carbonate, e.g. di-tert. butyldicarbonate preferably at room temperature to give e.g. the bis-Boc-derivative.

Step G: A branched alkyl with a tertiary hydroxyl moiety is introduced on the piperidinone ring of the bis-protected piperidinone of formula (XX) to form the hydroxyl alkyl substituted piperidinone derivative of formula (XXI) wherein $R_1$, $R_2$, $R_3$, $R_7$ and $R_8$ have meanings as defined herein. Typically the bis-Boc-derivative is treated with a strong base such as LiHMDS to deliver the enolate, e.g. the Li-enolate. This reaction is performed in a suitable solvent, e.g, in THF, preferably at temperatures below 0° C., preferably –78° C. The enolate can then be treated preferably at that temperature with $BF_3$-diethyletherate followed by a suitable ketone, e.g. acetone, to give the adduct as a crystalline residue after work up and crystallization from hexane.

Step H: The hydroxyl alkyl substituted piperidinone derivative of formula (XXI) is converted into the piperidinone derivative with an exocyclic double bond of formula (XXII) wherein $R_1$, $R_2$, $R_3$, $R_7$ and $R_8$ have meanings as defined herein. Preferably, the teriary alcohol is treated in a solvent, e.g. dichloromethane, with a base, e.g. an amine base such as triethylamine, as well as methanesulphonyl chloride to give a mixture of e.g. "iso propylidene" and "propenyliden" product (XXII) depending on the nature of $R_4$. The reaction is carried out by preferably –10 to 15° C., more preferably –5° C.

Step I: Double bond isomerisation of the exocyclic double bond of the piperidinone derivative of formula (XXII) yields the olefin of formula (XXIII) wherein $R_1$, $R_2$, $R_3$, $R_7$ and $R_8$ have meanings as defined herein. Preferably, a solution of the propenyliden compound (XXII) or the like depending on the nature of $R_4$, or a mixture of both compounds as obtained in step H is treated with a base (e.g. $NEt_3$ or DBU) in ethyl acetate at room temperature to perform the double bond isomerisation to the desired isopropylidene compound.

Step J: The olefin of formula (XXIII) is hydrogenated to obtain the alkyl substituted piperidinone derivative of formula (XXIV) wherein $R_1$, $R_2$, $R_3$, $R_7$ and $R_8$ have meanings as defined herein. Preferably, the olefin of formula (XXIII) is hydrogenated in a suitable solvent e.g. ethyl acetate, in the presence of small amounts of a base, e.g. an amine base such as triethylamine, over Pt—C. This reaction is preferably conducted at elevated temperatures and pressure or until the conversion is complete. Temperatures of 30-70° C., e.g. at 50° C. are preferred. A pressure of 2-10 bar, e.g. 5 bar, is preferred.

Step K: Ring opening of the piperidinone derivative of formula (XXIV) gives a γ-hydroxy acid intermediate which is subjected to lactonisation to provide compound of formula (XI) wherein $R_1$, $R_2$, $R_3$ and $R_8$ have meanings as defined herein. Preferably, the compound from the hydrogenation step above is treated first with a base, e.g. an inorganic base such as NaOH to yield the γ-hydroxy acid intermediate. More preferably, an aqueous solution, e.g. 2N, of sodium hydroxide is used. A suitable cosolvent such as THF may be present. Preferably, a phase transfer catalyst (e.g. TEBA-Cl) may also be present. The reaction is preferably conducted at 20-60° C., more preferably at 40° C. The obtained y-hydroxy acid, e.g. in the form of he sodium salt, is then treated with acid, e.g. glacial acetic acid, to perform the lactonisation. The acid is typically used in excess.

Finally, compounds of formula (XI) may be converted to compounds of formula (A) wherein $R_1$, $R_2$, $R_3$, $R_4$ and $R_5$ are as defined herein above, by carrying out the remaining steps using reaction conditions as described herein in the Examples, or according to methods well known in the art, see e.g. EP-A-0678 503. Specifically, treatment with an amine $H_2NR_5$ wherein $R_5$ is as defined herein above leads to lactone ring opening of the compound of formula (XI) by to afford the amide of formula (XIII). This is typically performed as illustrated herein in the Examples, or using methods well known in the art, see e.g. EP-A-0678 503. Finally, compounds of formula (XIII) may be converted to compounds of formula (A) wherein $R_1$, $R_2$, $R_3$, $R_4$ and $R_5$ are as defined herein above, by removal of the N-protecting group of the compound of formula (XIII) to reveal the free amine, using standard protecting group chemistry following the procedures as described in the literature referenced below, and optionally salt formation to obtain the compound of formula (A) using reaction conditions as described herein in the Examples. Typical salt formation procedures are e.g. described in U.S. Pat. No. 5,559,111. These final steps are illustrated in Scheme 5.

Scheme 5: Final steps for a method for preparing a compound of formula (A) starting from compound of formula (XI).

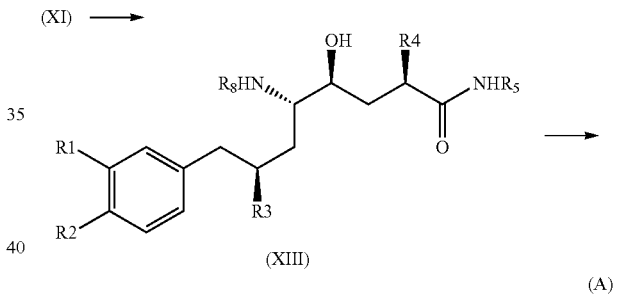

Alternatively, compounds of formula (X) can be prepared by the following steps. The carboxylic acid group of the compound of formula (X) is reacted with an amine $H_2NR_5$ wherein $R_5$ is as defined herein above, using peptide coupling to afford the amide of formula (XII) according to well known literature and textbook procedures, see e.g. Houben-Weyl, Methoden der Organische Chemie, $4^{th}$ Ed, Synthese von Peptiden 1.

Subsequent stereoselective reduction of the C4-carbonyl group of the compound of formula (XII) affords the compound of formula (XIII). Reference is made e.g. to R. V. Hoffman et al. JOC, 67, 1045 (2002) and lit. cited therein & R. V. Hoffman et al., JOC, 62, 2292 (1997), M. T. Reetz et al, Chem. Commun. (1989), 1474. Finally, compounds of formula (XIII) may be converted to compounds of formula (A) wherein $R_1$, $R_2$, $R_3$, $R_4$ and $R_5$ are as defined herein above, by removal of the N-protecting group of compound (XIII) to reveal the free amine, using standard protecting group chemistry following the procedures as described in the literature referenced below, and optionally salt formation to obtain the compound of formula (A) using reaction conditions as described herein in the Examples Typical salt formation procedures are e.g. described in U.S. Pat. No. 5,559,111.

Other objects, features, advantages and aspects of the present invention will become apparent to those skilled in the art from the following description, appended Examples and claims. It should be understood, however, that the description, appended claims, while indicating preferred embodiments of the invention, are given by way of illustration only. Various changes and modifications within the spirit and scope of the disclosed invention will become readily apparent to those skilled in the art from reading the following.

Listed below are definitions of various terms used to describe the compounds of the instant invention. These definitions apply to the terms as they are used throughout the specification unless they are otherwise limited in specific instances either individually or as part of a larger group. Any definition for one substituent can be combined with any other definition for another substituent, including in both instances preferred definitions.

$R_1$ is halogen, $C_{1-6}$halogenalkyl, $C_{1-6}$alkoxy-$C_{1-6}$alkyloxy or $C_{1-6}$alkoxy-$C_{1-6}$alkyl. Preferred embodiments are described below.

$R_2$ is halogen, $C_{1-4}$alkyl or $C_{1-4}$alkoxy. Preferred embodiments are described below.

$R_3$ and $R_4$ are independently branched $C_{3-6}$alkyl. Preferred embodiments are described below.

$R_5$ is cycloalkyl, $C_{1-6}$alkyl, $C_{1-6}$hydroxyalkyl, $C_{1-6}$alkoxy-$C_{1-6}$alkyl, $C_{1-6}$alkanoyloxy-$C_{1-6}$alkyl, $C_{1-6}$aminoalkyl, $C_{1-6}$alkylamino-$C_{1-6}$alkyl, $C_{1-6}$dialkylamino-$C_{1-6}$alkyl, $C_{1-6}$alkanoylamino-$C_{1-6}$alkyl, HO(O)C—$C_{1-6}$alkyl, $C_{1-6}$alkyl-O—(O)C—$C_{1-6}$alkyl, $H_2$N—C(O)—$C_{1-6}$alkyl, $C_{1-6}$alkyl-HN—C(O)—$C_{1-6}$alkyl or $(C_{1-6}$alkyl$)_2$N—C(O)—$C_{1-6}$alkyl. Preferred embodiments are described below.

$R_6$ is $C_{1-20}$alkyl, $C_{3-12}$cycloalkyl, $C_{3-12}$cycloalkyl-$C_{1-6}$alkyl, $C_{6-10}$aryl or $C_{6-10}$aryl-$C_{1-6}$alkyl. Preferred embodiments are described below.

$R_7$ is a suitable O-protecting group as known in the art. Examples include $C_{1-6}$alkyl, $C_{1-6}$alkoxy-$C_{1-6}$alkyloxy, $C_{6-10}$aryl-$C_{1-6}$alkyl, $C_{1-6}$alkoxy-carbonyl, $C_{6-10}$aryl-$C_{1-6}$alkoxycarbonyl or $(C_{1-8}$alkyl$)_3$silyl. Preferred embodiments are described below.

$R_8$ is a suitable N-protecting group as known in the art. An N-protecting group is, for example, an amino protecting group which is conventionally used in peptide chemistry (cf.: "Protective groups in Organic Synthesis", $5^{th}$. Ed. T. W. Greene & P. G. M. Wuts), especially in chemistry of protecting pyrrolidines.

Preferred protecting groups comprise, for example, (i) $C_1$-$C_2$-alkyl that is mono-, di- or trisubstituted by phenyl, such as benzyl, (or) benzhydryl or trityl, wherein the phenyl ring is unsubstituted or substituted by one or more, e.g. two or three, residues e.g. those selected from the group consisting of $C_1$-$C_7$-alkyl, hydroxy, $C_1$-$C_7$-alkoxy, $C_2$-$C_8$-alkanoyl-oxy, halogen, nitro, cyano, and $CF_3$; phenyl-C1-C2-alkoxycarbonyl; and allyl or cinnamyl. Especially preferred are benzyloxycarbonyl (Cbz), 9-fluorenylmethyloxycarbony (Fmoc), benzyloxymethyl (BOM), pivaloyl-oxy-methyl (POM), trichloroethxoycarbonyl (Troc), 1-adamantyloxycarbonxyl (Adoc), but can also be benzyl, cumyl, benzhydryl, trityl, allyl, alloc (allyloxycarbonyl). The protecting group can also be silyl, like trialklysilyl, especially trimethylsilyl, tert.-butyl-dimethylsilyl, triethylsilyl, triisopropylsilyl, trimethylsilyethoxymethyl (SEM), and can also be substituted sulfonyl or substituted sulfenyl.

Examples for $R_8$ include $C_{6-10}$aryl-$C_{1-6}$alkyl, and $C_{1-6}$alkyl-carbonyl, $C_{6-10}$aryl-carbonyl, $C_{1-6}$alkoxy-carbonyl, and $C_{6-10}$aryl-$C_{1-6}$alkoxycarbonyl. Further preferred embodiments are described below.

$R_9$ is $C_{1-20}$alkyl, $C_{3-12}$cycloalkyl, $C_{3-12}$cycloalkyl-$C_{1-6}$alkyl, $C_{6-10}$aryl, $C_{2-20}$alkenyl or $C_{6-10}$aryl-$C_{1-6}$alkyl. In one embodiment $R_9$ is $C_{1-20}$alkyl, $C_{3-12}$cycloalkyl, $C_{3-12}$cycloalkyl-$C_{1-6}$alkyl, $C_{6-10}$aryl or $C_{6-10}$aryl-$C_{1-6}$alkyl. Preferred embodiments are described below.

As an alkyl, $R_1$ and $R_2$ may be linear or branched and preferably comprise 1 to 6 C atoms, especially 1 or 4 C atoms. Examples are methyl, ethyl, n- and i-propyl, n-, i- and t-butyl, pentyl and hexyl.

As a halogenalkyl, $R_1$ may be linear or branched and preferably comprise 1 to 4 C atoms, especially 1 or 2 C atoms. Examples are fluoromethyl, difluoromethyl, trifluoromethyl, chloromethyl, dichloromethyl, trichloromethyl, 2-chloroethyl and 2,2,2-trifluoroethyl.

As an alkoxy, $R_1$ and $R_2$ may be linear or branched and preferably comprise 1 to 4 C atoms. Examples are methoxy, ethoxy, n- and i-propyloxy, n-, i- and t-butyloxy, pentyloxy and hexyloxy.

As an alkoxyalkyl, $R_1$ may be linear or branched. The alkoxy group preferably comprises 1 to 4 and especially 1 or 2 C atoms, and the alkyl group preferably comprises 1 to 4 C atoms. Examples are methoxymethyl, 2-methoxyethyl, 3-methoxypropyl, 4-methoxybutyl, 5-methoxypentyl, 6-methoxyhexyl, ethoxymethyl, 2ethoxyethyl, 3-ethoxypropyl, 4-ethoxybutyl, 5-ethoxypentyl, 6-ethoxyhexyl, propyloxymethyl, butyloxymethyl, 2-propyloxyethyl and 2-butyloxyethyl.

As a $C_{1-6}$alkoxy-$C_{1-6}$alkyloxy, $R_1$ and $R_7$ may be linear or branched. The alkoxy group preferably comprises 1 to 4 and especially 1 or 2 C atoms, and the alkyloxy group preferably comprises 1 to 4 C atoms. Examples are methoxymethyloxy, 2-methoxyethyloxy, 3-methoxypropyloxy, 4-methoxybutyloxy, 5-methoxypentyloxy, 6-methoxyhexyloxy, ethoxymethyloxy, 2-ethoxyethyloxy, 3-ethoxypropyloxy, 4-ethoxybutyloxy, 5-ethoxypentyloxy, 6-ethoxyhexyloxy, propyloxymethyloxy, butyloxymethyloxy, 2-propyloxyethyloxy and 2-butyloxyethyloxy.

As a branched alkyl, $R_3$ and $R_4$ preferably comprise 3 to 6 C atoms. Examples are i-propyl, and t-butyl, and branched isomers of pentyl and hexyl.

As a cycloalkyl, $R_5$ may preferably comprise 3 to 8 ring-carbon atoms, 3 or 5 being especially preferred. Some examples are cyclopropyl, cyclobutyl, cyclopentyl, cyclohexyl and cyclooctyl. The cycloalkyl may optionally be substituted by one or more substituents, such as alkyl, halo, oxo, hydroxy, alkoxy, amino, alkylamino, dialkylamino, thiol, alkylthio, nitro, cyano, heterocyclyl and the like.

As an alkyl, $R_5$ may be linear or branched in the form of alkyl and preferably comprise 1 to 6 C atoms. Examples of alkyl are listed herein above. Methyl, ethyl, n- and i-propyl, n-, and t-butyl are preferred.

As a $C_{1-6}$hydroxyalkyl, $R_5$ may be linear or branched and preferably comprise 2 to 6 C atoms. Some examples are 2-hydroxyethyl, 2-hydroxypropyl, 3-hydroxypropyl, 2-, 3- or 4-hydroxybutyl, hydroxypentyl and hydroxyhexyl.

As a $C_{1-6}$alkoxy-$C_{1-6}$alkyl, $R_5$ may be linear or branched. The alkoxy group preferably comprises 1 to 4 C atoms and the alkyl group preferably 2 to 4 C atoms. Some examples are 2-methoxyethyl, 2-methoxypropyl, 3-methoxypropyl, 2-, 3- or 4-methoxybutyl, 2-ethoxyethyl, 2-ethoxypropyl, 3-ethoxypropyl, and 2-, 3- or 4-ethoxybutyl.

As a $C_{1-6}$alkanoyloxy-$C_{1-6}$alkyl, $R_5$ may be linear or branched. The alkanoyloxy group preferably comprises 1 to 4 C atoms and the alkyl group preferably 2 to 4 C atoms. Some examples are formyloxymethyl, formyloxyethyl, acetyloxyethyl, propionyloxyethyl and butyroyloxyethyl.

As a $C_{1-6}$aminoalkyl, $R_5$ may be linear or branched and preferably comprise 2 to 4 C atoms. Some examples are 2-aminoethyl, 2- or 3-aminopropyl and 2-, 3- or 4-aminobutyl.

As $C_{1-6}$alkylamino-$C_{1-6}$alkyl and $C_{1-6}$dialkylamino-$C_{1-6}$alkyl, $R_5$ may be linear or branched. The alkylamino group preferably comprises $C_{1-4}$alkyl groups and the alkyl group has preferably 2 to 4 C atoms. Some examples are 2-methylaminoethyl, 2-dimethylaminoethyl, 2-ethylaminoethyl, 2-ethylaminoethyl, 3-methylaminopropyl, 3-dimethylaminopropyl, 4-methylaminobutyl and 4-dimethylaminobutyl.

As a HO(O)C—$C_{1-6}$alkyl, $R_5$ may be linear or branched and the alkyl group preferably comprises 2 to 4 C atoms. Some examples are carboxymethyl, carboxyethyl, carboxypropyl and carboxybutyl.

As a $C_{1-6}$alkyl-O—(O)C—$C_{1-6}$alkyl, $R_5$ may be linear or branched, and the alkyl groups preferably comprise independently of one another 1 to 4 C atoms. Some examples are methoxycarbonylmethyl, 2-methoxycarbonylethyl, 3-methoxycarbonylpropyl, 4-methoxycarbonylbutyl, ethoxycarbonylmethyl, 2-ethoxycarbonylethyl, 3-ethoxycarbonylpropyl, and 4-ethoxycarbonylbutyl.

As a $H_2N$—C(O)—$C_{1-6}$alkyl, $R_5$ may be linear or branched, and the alkyl group preferably comprises 2 to 6 C atoms. Some examples are carbamidomethyl, 2-carbamidoethyl, 2-carbamido-2,2-dimethylethyl, 2- or 3-carbamidopropyl, 2-, 3- or 4-carbamidobutyl, 3-carbamido-2-methylpropyl, 3-carbamido-1,2-dimethylpropyl, 3-carbamido-3-ethylpropyl, 3-carbamido-2,2-dimethylpropyl, 2-, 3-, 4- or 5-carbamidopentyl, 4-carbamido-3,3- or -2,2-dimethylbutyl.

As a $C_{1-6}$alkyl-HN—C(O)—$C_{1-6}$alkyl or ($C_{1-6}$alkyl)$_2$N—C(O)—$C_{1-6}$alkyl, $R_5$ may be linear or branched, and the NH-alkyl group preferably comprises 1 to 4 C atoms and the alkyl group preferably 2 to 6 C atoms. Examples are the carbamidoalkyl groups defined herein above, whose N atom is substituted, with one or two methyl, ethyl, propyl or butyl.

As an alkyl, $R_6$, $R_7$, $R_9$ and $R_{10}$ may be linear or branched and comprise preferably 1 to 12 C atoms, 1 to 8 C atoms being especially preferred. Particularly preferred is a linear $C_{1-4}$alkyl. Some examples are methyl, ethyl and the isomers of propyl, butyl, pentyl, hexyl, heptyl, octyl, nonyl, decyl, undecyl, dodecyl, tetradecyl, hexadecyl, octacyl and eicosyl. Especially preferred are methyl and ethyl.

As a cycloalkyl, $R_6$, $R_9$ and $R_{10}$ may preferably comprise 3 to 8 ring-carbon atoms, 5 or 6 being especially preferred. Some examples are cyclopropyl, cyclobutyl, cyclopentyl, cyclohexyl, cyclooctyl and cyclododecyl.

As a cycloalkyl-alkyl, $R_6$, $R_9$ and $R_{10}$ may comprise preferably 4 to 8 ring-carbon atoms, 5 or 6 being especially preferred, and preferably 1 to 4 C atoms in the alkyl group, 1 or 2 C atoms being especially preferred. Some examples are cyclopropylmethyl, cyclobutylmethyl, cyclopentylmethyl or cyclopentylethyl, and cyclohexylmethyl or 2-cyclohexylethyl.

As an alkoxycarbonyl, $R_7$ and $R_8$ may comprise a linear or branched alkyl group which preferably comprises 1 to 4 C atoms. Examples are methoxy, ethoxy, n- and i-propyloxy, n-, i- and t-butyloxy, pentyloxy and hexyloxy.

As an arylalkoxycarbonyl, $R_7$ and $R_8$ may comprise a linear or branched alkyl group which preferably comprises 1 to 4 C atoms and an aryl moiety, preferably phenyl. An example includes benzyloxycarbonyl.

As an alkenyl, $R_9$ may be linear or branched alkyl containing a double bond and comprising preferably 2 to 12 C atoms, 2 to 8 C atoms being especially preferred. Particularly preferred is a linear $C_{2-4}$alkenyl. Some examples of alkyl groups are ethyl and the isomers of propyl, butyl, pentyl, hexyl, heptyl, octyl, nonyl, decyl, undecyl, dodecyl, tetradecyl, hexadecyl, octacyl and eicosyl, each of which containing a double bond. Especially preferred is allyl.

As an aryl, $R_6$, $R_9$ and $R_{10}$ are preferably phenyl or naphthyl.

As an aralkyl, $R_6$, $R_7$, $R_8$, $R_9$ and $R_{10}$ are preferably benzyl or phenethyl.

In a preferred embodiment, $R_1$ is $C_{1-6}$alkoxy-$C_{1-6}$alkyloxy as defined above, more preferably methoxy- or ethoxy-$C_{1-4}$alkyloxy.

In a preferred embodiment, $R_2$ is alkoxy as defined above, more preferably methoxy or ethoxy.

In a preferred embodiment, $R_1$ is methoxy- or ethoxy-$C_{1-4}$alkyloxy, and $R_2$ is preferably methoxy or ethoxy. Particularly preferred are compounds of formula (A), wherein $R_1$ is 3-methoxypropyloxy and $R_2$ is methoxy.

In a preferred embodiment, $R_3$ and $R_4$ are in each case i-propyl.

In a preferred embodiment, $R_5$ is $H_2N$—C(O)—$C_{1-6}$alkyl, $C_{1-6}$alkyl-HN—C(O)—$C_{1-6}$alkyl or ($C_{1-6}$alkyl)$_2$N—C(O)—$C_{1-6}$alkyl, with the preferred examples as described above, more preferably is $H_2N$—C(O)—$C_{1-6}$alkyl, most preferably carbamido-2,2-dimethylethyl.

In a preferred embodiment, $R_6$ is $C_{1-6}$alkyl, more preferably $C_{1-4}$alkyl, most preferably methyl or ethyl.

In a preferred embodiment, $R_7$ and $R_8$ are independently arylalkoxycarbonyl, alkoxycarbonyl, or aralkyl such as benzyl, t-butoxycarbonyl or benzyloxycarbonyl.

In a preferred embodiment, $R_7$ and $R_8$ are independently t-butoxy- or benzyloxycarbonyl.

In a preferred embodiment, $R_9$ is $C_{1-6}$alkyl or $C_{6-10}$aryl-$C_{1-4}$alkyl, more preferably $C_{1-4}$ alkyl or benzyl, most preferably methyl, ethyl, t-butyl or benzyl.

Accordingly, preferred are the methods of the present invention, wherein a compound of formula (A) has the formula

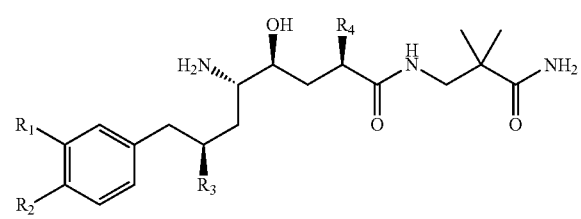

(B)

wherein $R_1$ is 3-methoxypropyloxy; $R_2$ is methoxy; and $R_3$ and $R_4$ are isopropyl; or a pharmaceutically acceptable salt thereof.

Further preferred are the methods of the present invention, wherein a compound of formula (B) is (2S,4S,5S,7S)-5-amino-4-hydroxy-2-isopropyl-7-[4-methoxy-3-(3-methoxypropoxy)-benzyl]-8-methyl-nonanoic acid (2-carbamoyl-2-methyl-propyl)-amide hemifumarate, also known as aliskiren.

The present invention also relates to the following key intermediates useful when preparing the compound of formula (A). Each of these key intermediates is an important synthetic building block for the synthesis of the compound of formula (A) both with respect to the functionality and the stereochemistry. Each of these key intermediates can be prepared by the steps as outlined in the respective schemes 1, 1a, 1b, 1c, 2 and 4 either taken alone or in an appropriate combination and by either following the respective complete route as outlined in the schemes. Alternatively, these key intermediates can be prepared by starting from any intermediate product obtainable at any of the stages as outlined in the schemes, including the preceding intermediate product and, thus, performing only one conversion to the respective key intermediate.

Compounds of the formula

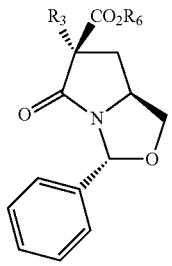

(IIc)

wherein $R_3$ is branched $C_{3-6}$alkyl, preferably i-propyl, and $R_6$ is $C_{1-20}$alkyl, $C_{3-12}$cycloalkyl, $C_{3-12}$cycloalkyl-$C_{1-6}$alkyl, $C_{6-10}$aryl or $C_{6-10}$aryl-$C_{1-6}$alkyl, preferably $C_{1-4}$alkyl, most preferably methyl or ethyl.

Compounds of the formula

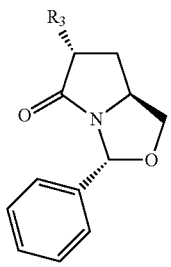

(IId)

wherein $R_3$ is branched $C_{3-6}$alkyl, preferably i-propyl.

Compounds of the formula

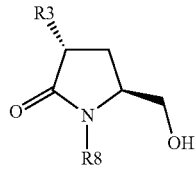

(IIg)

wherein $R_3$ is branched $C_{3-6}$alkyl, preferably i-propyl, and $R_8$ is an N-protecting group, e.g. $C_{6-10}$aryl-$C_{1-6}$alkyl, $C_{1-6}$alkyl-carbonyl, $C_{6-10}$aryl-carbonyl, $C_{1-6}$alkoxy-carbonyl, or $C_{6-10}$aryl-$C_{1-6}$alkoxycarbonyl.

Compounds of the formula

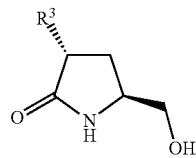

(III)

wherein $R_3$ is branched $C_{3-6}$alkyl, preferably i-propyl.

Compounds of the formula

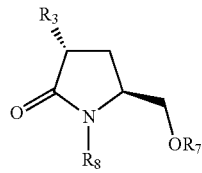

(IV)

wherein $R_3$ is branched $C_{3-6}$alkyl, preferably i-propyl; $R_7$ is an O-protecting group, e.g. $C_{1-6}$alkyl, $C_{1-6}$alkoxy-$C_{1-6}$alkyloxy, $C_{6-10}$aryl-$C_{1-6}$alkyl, $C_{1-6}$alkoxy-carbonyl, $C_{6-10}$aryl-$C_{1-6}$alkoxycarbonyl or $(C_{1-8}$alkyl$)_3$silyl; and $R_8$ is an N-protecting group, e.g. $C_{6-10}$aryl-$C_{1-6}$alkyl, $C_{1-6}$alkyl-carbonyl, $C_{6-10}$aryl-carbonyl, $C_{1-6}$alkoxy-carbonyl, or $C_{6-10}$aryl-$C_{1-6}$alkoxycarbonyl.

Compounds of the formula

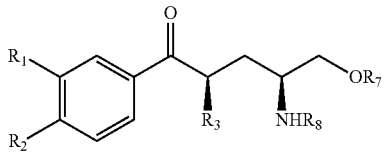

(V)

wherein $R_1$ is halogen, $C_{1-6}$halogenalkyl, $C_{1-6}$alkoxy-$C_{1-6}$alkyloxy or $C_{1-6}$alkoxy-$C_{1-6}$alkyl; $R_2$ is halogen, $C_{1-4}$alkyl or $C_{1-4}$alkoxy; $R_3$ is branched $C_{3-6}$alkyl; $R_7$ is $C_{1-6}$alkyl, $C_{1-6}$alkoxy-$C_{1-6}$alkyloxy, $C_{6-10}$aryl-$C_{1-6}$alkyl, $C_{1-6}$alkoxy-carbonyl, $C_{6-10}$aryl-$C_{1-6}$alkoxycarbonyl or $(C_{1-8}$alkyl$)_3$silyl; and $R_8$ is $C_{6-10}$aryl-$C_{1-6}$alkyl, $C_{1-6}$alkyl-carbonyl, $C_{6-10}$aryl-carbonyl, $C_{1-6}$alkoxy-carbonyl, $C_{6-10}$aryl-$C_{1-6}$alkoxycarbonyl; are useful intermediates for the preparation of compounds of formula (A).

Preferred are the compounds of formula (V) having the formula

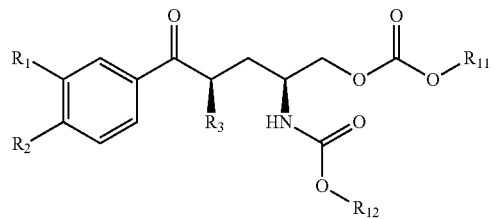

(V')

wherein $R_1$ is 3-methoxypropyloxy; $R_2$ is methoxy; $R_3$ is isopropyl; and $R_{11}$ and $R_{12}$ are independently t-butyl or benzyl.

Preferred are the compounds of formula (V') wherein $R_{11}$ and $R_{12}$ are t-butyl.

Compounds of the formula

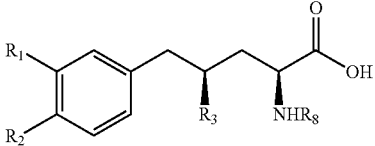

(VII)

wherein $R_1$ is halogen, $C_{1-6}$halogenalkyl, $C_{1-6}$alkoxy-$C_{1-6}$alkyloxy or $C_{1-6}$alkoxy-$C_{1-6}$alkyl; $R_2$ is halogen, $C_{1-4}$alkyl or $C_{1-4}$alkoxy; $R_3$ is branched $C_{3-6}$alkyl; and $R_8$ is $C_{6-10}$aryl-$C_{1-6}$alkyl, $C_{1-6}$alkyl-carbonyl, $C_{6-10}$aryl-carbonyl, $C_{1-6}$alkoxy-carbonyl, $C_{8-10}$aryl-$C_{1-6}$alkoxycarbonyl; are also useful intermediates for the preparation of compounds of formula (A).

Preferred are the compounds of formula (VII) having the formula

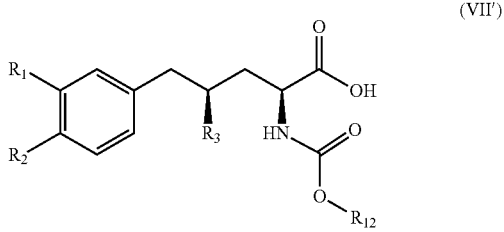

(VII')

wherein $R_1$ is 3-methoxypropyloxy; $R_2$ is methoxy; $R_3$ is isopropyl; and $R_{12}$ is t-butyl or benzyl.

Preferred are the compounds of formula (VII') wherein $R_{12}$ is t-butyl.

Compounds of the formula

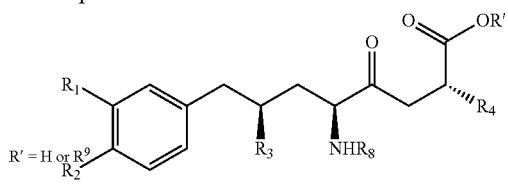

wherein $R_1$ is halogen, $C_{1-6}$halogenalkyl, $C_{1-6}$alkoxy-$C_{1-6}$alkyloxy or $C_{1-6}$alkoxy-$C_{1-6}$alkyl; $R_2$ is halogen, $C_{1-4}$alkyl or $C_{1-4}$alkoxy; $R_3$ and $R_4$ are independently branched $C_{3-6}$alkyl; $R_8$ is $C_{8-10}$aryl-$C_{1-6}$alkyl, $C_{1-6}$alkyl-carbonyl, $C_{6-10}$aryl-carbonyl, $C_{1-6}$alkoxy-carbonyl, $C_{6-10}$aryl-$C_{1-6}$ alkoxycarbonyl; and $R_9$ is $C_{1-20}$alkyl, $C_{3-12}$cycloalkyl, $C_{3-12}$cycloalkyl-$C_{1-6}$alkyl, $C_{6-10}$aryl, $C_{2-20}$alkenyl or $C_{8-10}$aryl-$C_{1-6}$alkyl, preferably $C_{1-6}$alkyl or $C_{6-10}$aryl-$C_{1-4}$ alkyl, preferably $C_{1-4}$ alkyl or benzyl.

Compounds of the formula

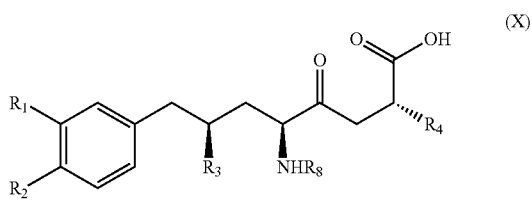

(X)

wherein $R_1$ is halogen, $C_{1-6}$halogenalkyl, $C_{1-6}$alkoxy-$C_{1-6}$alkyloxy or $C_{1-6}$alkoxy-$C_{1-6}$alkyl; $R_2$ is halogen, $C_{1-4}$alkyl or $C_{1-4}$alkoxy; $R_3$ and $R_4$ are independently branched $C_{3-8}$alkyl; and $R_8$ is $C_{6-10}$aryl-$C_{1-6}$alkyl, $C_{1-6}$alkyl-carbonyl, $C_{8-10}$aryl-carbonyl, $C_{1-6}$alkoxy-carbonyl, $C_{6-10}$aryl-$C_{1-6}$ alkoxycarbonyl; are also useful intermediates for the preparation of compounds of formula (A).

Preferred are the compounds of formula (X) having the formula

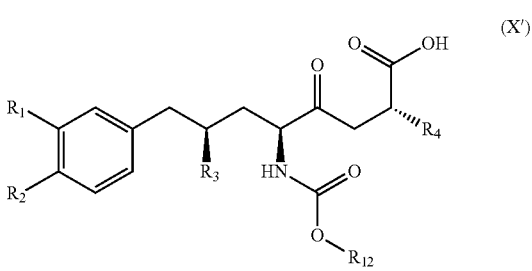

(X')

wherein $R_1$ is 3-methoxypropyloxy; $R_2$ is methoxy; $R_3$ is isopropyl; $R_4$ is isopropyl; and $R_{12}$ is t-butyl or benzyl.

Preferred are the compounds of formula (X') wherein $R_{12}$ is t-butyl.

Compounds of the formula

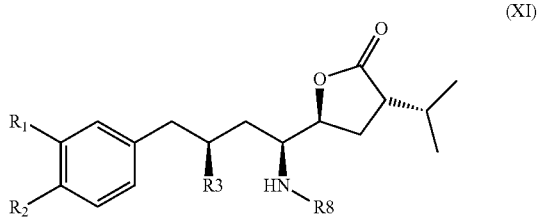

(XI)

wherein $R_1$ is halogen, $C_{1-6}$halogenalkyl, $C_{1-6}$alkoxy-$C_{1-6}$alkyloxy or $C_{1-6}$alkoxy-$C_{1-6}$alkyl, preferably 3-methoxypropyloxy; $R_2$ is halogen, $C_{1-4}$alkyl or $C_{1-4}$alkoxy, preferably methoxy; $R_3$ and $R_4$ are independently branched $C_{3-6}$alkyl, preferably each isopropyl; and $R_8$ is an N-protecting group, e.g. $C_{6-10}$aryl-$C_{1-6}$alkyl, $C_{1-6}$alkyl-carbonyl, $C_{6-10}$aryl-carbonyl, $C_{1-6}$alkoxy-carbonyl, or $C_{6-10}$aryl-$C_{1-6}$ alkoxycarbonyl.

Compounds of the formula

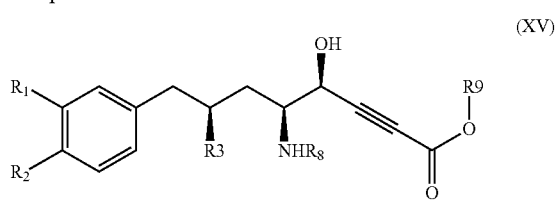

(XV)

wherein $R_1$ is halogen, $C_{1-6}$halogenalkyl, $C_{1-6}$alkoxy-$C_{1-6}$alkyloxy or $C_{1-6}$alkoxy-$C_{1-6}$alkyl, preferably 3-methoxypropyloxy; $R_2$ is halogen, $C_{1-4}$alkyl or $C_{1-4}$alkoxy, preferably methoxy; $R_3$ is branched $C_{3-6}$alkyl, preferably isopropyl; and $R_8$ is an N-protecting group, e.g. $C_{6-10}$aryl-$C_{1-6}$alkyl, $C_{1-6}$alkyl-carbonyl, $C_{6-10}$aryl-carbonyl, $C_{1-6}$alkoxy-carbonyl, or $C_{6-10}$aryl-$C_{1-6}$alkoxycarbonyl; $R_9$ is $C_{1-20}$alkyl, $C_{3-12}$cycloalkyl, $C_{3-12}$cycloalkyl-$C_{1-6}$alkyl, $C_{6-10}$aryl, $C_{2-20}$alkenyl or $C_{6-10}$aryl-$C_{1-6}$alkyl, preferably $C_{1-6}$alkyl or $C_{6-10}$aryl-$C_{1-4}$alkyl, preferably $C_{1-4}$ alkyl or benzyl.

Compounds of the formula

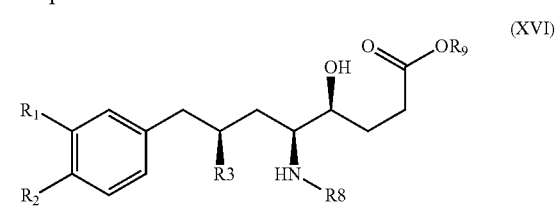

(XVI)

wherein $R_1$ is halogen, $C_{1-6}$halogenalkyl, $C_{1-6}$alkoxy-$C_{1-6}$alkyloxy or $C_{1-6}$alkoxy-$C_{1-6}$alkyl, preferably 3-methoxypropyloxy; $R_2$ is halogen, $C_{1-4}$alkyl or $C_{1-4}$alkoxy, preferably methoxy; $R_3$ is branched $C_{3-6}$alkyl, preferably isopropyl; and $R_8$ is an N-protecting group, e.g. $C_{6-10}$aryl-$C_{1-6}$alkyl, $C_{1-6}$alkyl-carbonyl, $C_{6-10}$aryl-carbonyl, $C_{1-6}$alkoxy-carbonyl, or $C_{6-10}$aryl-$C_{1-6}$alkoxycarbonyl; $R_9$ is $C_{1-20}$alkyl, $C_{3-12}$cycloalkyl, $C_{3-12}$cycloalkyl-$C_{1-6}$alkyl, $C_{6-10}$aryl, $C_{2-20}$alkenyl or $C_{6-10}$aryl-$C_{1-6}$alkyl, preferably $C_{1-6}$alkyl or $C_{6-10}$aryl-$C_{1-4}$alkyl, preferably $C_{1-4}$ alkyl or benzyl.

Compounds of the formula

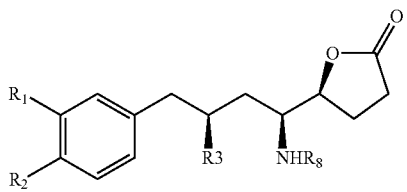
(XVII)

wherein $R_1$ is halogen, $C_{1-6}$halogenalkyl, $C_{1-6}$alkoxy-$C_{1-6}$alkyloxy or $C_{1-6}$alkoxy-$C_{1-6}$alkyl, preferably 3-methoxypropyloxy; $R_2$ is halogen, $C_{1-4}$alkyl or $C_{1-4}$alkoxy, preferably methoxy; $R_3$ is branched $C_{3-6}$alkyl, preferably isopropyl; and $R_8$ is an N-protecting group, e.g. $C_{6-10}$aryl-$C_{1-6}$alkyl, $C_{1-6}$alkyl-carbonyl, $C_{6-10}$aryl-carbonyl, $C_{1-6}$alkoxy-carbonyl, or $C_{6-10}$aryl-$C_{1-6}$alkoxycarbonyl.

Compounds of the formula

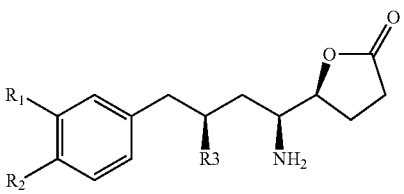
(XVIII)

wherein $R_1$ is halogen, $C_{1-6}$halogenalkyl, $C_{1-6}$alkoxy-$C_{1-6}$alkyloxy or $C_{1-6}$alkoxy-$C_{1-6}$alkyl, preferably 3-methoxypropyloxy; $R_2$ is halogen, $C_{1-4}$alkyl or $C_{1-4}$alkoxy, preferably methoxy; $R_3$ is branched $C_{3-6}$alkyl, preferably isopropyl.

Compounds of the formula

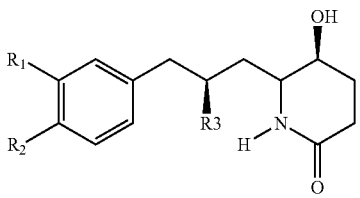
(XIX)

wherein $R_1$ is halogen, $C_{1-6}$halogenalkyl, $C_{1-6}$alkoxy-$C_{1-6}$alkyloxy or $C_{1-6}$alkoxy-$C_{1-6}$alkyl, preferably 3-methoxypropyloxy; $R_2$ is halogen, $C_{1-4}$alkyl or $C_{1-4}$alkoxy, preferably methoxy; $R_3$ is branched $C_{3-6}$alkyl, preferably isopropyl.

Compounds of the formula

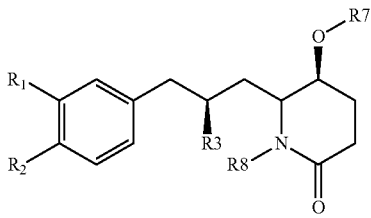
(XX)

wherein $R_1$ is halogen, $C_{1-6}$halogenalkyl, $C_{1-6}$alkoxy-$C_{1-6}$alkyloxy or $C_{1-6}$alkoxy-$C_{1-6}$alkyl, preferably 3-methoxypropyloxy; $R_2$ is halogen, $C_{1-4}$alkyl or $C_{1-4}$alkoxy, preferably methoxy; $R_3$ is branched $C_{3-6}$alkyl, preferably isopropyl; $R_7$ is an O-protecting group, e.g. $C_{1-6}$alkyl, $C_{1-6}$alkoxy-$C_{1-6}$alkyloxy, $C_{6-10}$aryl-$C_{1-6}$alkyl, $C_{1-6}$alkoxy-carbonyl, $C_{6-10}$aryl-$C_{1-6}$alkoxycarbonyl or $(C_{1-8}$alkyl$)_3$silyl; and $R_8$ is an N-protecting group, e.g. $C_{6-10}$aryl-$C_{1-6}$alkyl, $C_{1-6}$alkyl-carbonyl, $C_{6-10}$aryl-carbonyl, $C_{1-6}$alkoxy-carbonyl, or $C_{6-10}$aryl-$C_{1-6}$alkoxycarbonyl.

Compounds of the formula

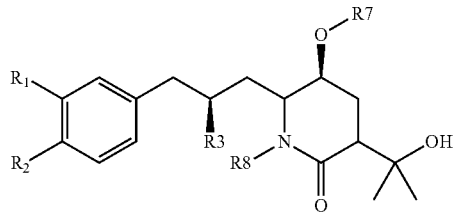
(XXI)

wherein $R_1$ is halogen, $C_{1-6}$halogenalkyl, $C_{1-6}$alkoxy-$C_{1-6}$alkyloxy or $C_{1-6}$alkoxy-$C_{1-6}$alkyl, preferably 3-methoxypropyloxy; $R_2$ is halogen, $C_{1-4}$alkyl or $C_{1-4}$alkoxy, preferably methoxy; $R_3$ is branched $C_{3-6}$alkyl, preferably isopropyl; $R_7$ is an O-protecting group, e.g. $C_{1-6}$alkyl, $C_{1-6}$alkoxy-$C_{1-6}$alkyloxy, $C_{6-10}$aryl-$C_{1-6}$alkyl, $C_{1-6}$alkoxy-carbonyl, $C_{6-10}$aryl-$C_{1-6}$alkoxycarbonyl or $(C_{1-8}$alkyl$)_3$silyl; and $R_8$ is an N-protecting group, e.g. $C_{6-10}$aryl-$C_{1-6}$alkyl, $C_{1-6}$alkyl-carbonyl, $C_{8-10}$aryl-carbonyl, $C_{1-6}$alkoxy-carbonyl, or $C_{6-10}$aryl-$C_{1-6}$alkoxycarbonyl.

Compounds of the formula

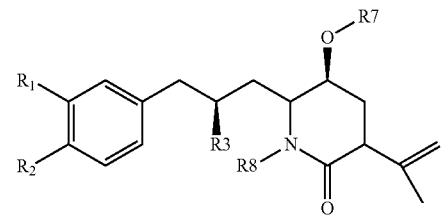
(XXII)

wherein $R_1$ is halogen, $C_{1-6}$halogenalkyl, $C_{1-6}$alkoxy-$C_{1-6}$alkyloxy or $C_{1-6}$alkoxy-$C_{1-6}$alkyl, preferably 3-methoxypropyloxy; $R_2$ is halogen, $C_{1-4}$alkyl or $C_{1-4}$alkoxy, preferably methoxy; $R_3$ is branched $C_{3-6}$alkyl, preferably isopropyl; $R_7$ is an O-protecting group, e.g. $C_{1-6}$alkyl, $C_{1-6}$alkoxy-$C_{1-6}$alkyloxy, $C_{6-10}$aryl-$C_{1-6}$alkyl, $C_{1-6}$alkoxy-carbonyl, $C_{6-10}$aryl-$C_{1-6}$alkoxycarbonyl or $(C_{1-8}$alkyl$)_3$silyl; and $R_8$ is an N-protecting group, e.g. $C_{6-10}$aryl-$C_{1-6}$alkyl, $C_{1-6}$alkyl-carbonyl, $C_{6-10}$aryl-carbonyl, $C_{1-6}$alkoxy-carbonyl, or $C_{6-10}$aryl-$C_{1-6}$alkoxycarbonyl.

Compounds of the formula

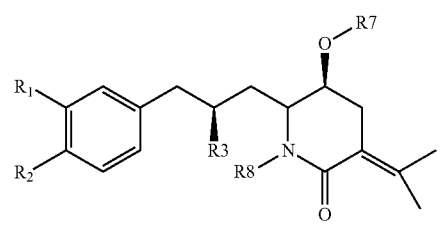
(XXIII)

wherein $R_1$ is halogen, $C_{1-6}$halogenalkyl, $C_{1-6}$alkoxy-$C_{1-6}$alkyloxy or $C_{1-6}$alkoxy-$C_{1-6}$alkyl, preferably 3-methoxypropyloxy; $R_2$ is halogen, $C_{1-4}$alkyl or $C_{1-4}$alkoxy, preferably methoxy; $R_3$ is branched $C_{3-6}$alkyl, preferably isopropyl; $R_7$ is an O-protecting group, e.g. $C_{1-6}$alkyl, $C_{1-6}$alkoxy-$C_{1-6}$alkyloxy, $C_{6-10}$aryl-$C_{1-6}$alkyl, $C_{1-6}$alkoxy-carbonyl, $C_{6-10}$aryl-$C_{1-6}$alkoxycarbonyl or $(C_{1-8}$alkyl$)_3$silyl; and $R_8$ is an N-protecting group, e.g. $C_{6-10}$aryl-$C_{1-6}$alkyl, $C_{1-6}$alkyl-carbonyl, $C_{6-10}$aryl-carbonyl, $C_{1-6}$alkoxy-carbonyl, or $C_{6-10}$aryl-$C_{1-6}$alkoxycarbonyl.

Compounds of the formula

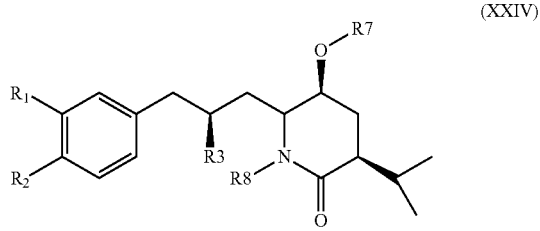

(XXIV)

wherein $R_1$ is halogen, $C_{1-6}$halogenalkyl, $C_{1-6}$alkoxy-$C_{1-6}$alkyloxy or $C_{1-6}$alkoxy-$C_{1-6}$alkyl, preferably 3-methoxypropyloxy; $R_2$ is halogen, $C_{1-4}$alkyl or $C_{1-4}$alkoxy, preferably methoxy; $R_3$ is branched $C_{3-6}$alkyl, preferably isopropyl; $R_7$ is an O-protecting group, e.g. $C_{1-6}$alkyl, $C_{1-6}$alkoxy-$C_{1-6}$alkyloxy, $C_{6-10}$aryl-$C_{1-6}$alkyl, $C_{1-6}$alkoxy-carbonyl, $C_{6-10}$aryl-$C_{1-6}$alkoxycarbonyl or $(C_{1-8}$alkyl$)_3$silyl; and $R_8$ is an N-protecting group, e.g. $C_{6-10}$aryl-$C_{1-6}$alkyl, $C_{1-6}$alkyl-carbonyl, $C_{6-10}$aryl-carbonyl, $C_{1-6}$alkoxy-carbonyl, or $C_{6-10}$aryl-$C_{1-6}$alkoxycarbonyl.

Moreover, the present invention is also directed to the chiral malonate derivative of formula (VIIIb) which is an important synthesis building block for the preparation of renin inhibitors:

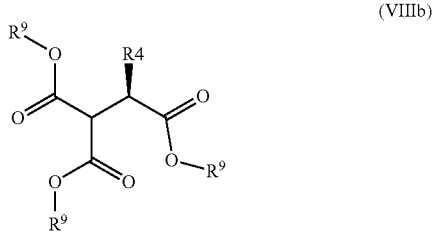

(VIIIb)

wherein $R^4$ and $R^9$ are as defined herein. Particularly preferred is the chiral malonate derivative of formula (VIII'b)

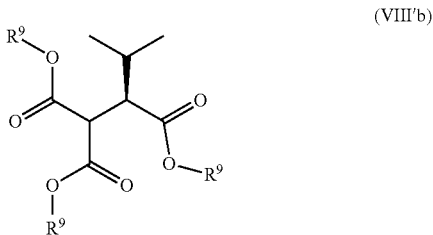

(VIII'b)

Preferably, the substituent $R^9$ is methyl or ethyl, most preferably methyl.

As indicated herein above, compounds of the present invention can be converted into acid addition salts. The acid addition salts may be formed with mineral acids, organic carboxylic acids or organic sulfonic acids, e.g., hydrochloric acid, fumaric acid and methanesulfonic acid, respectively.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The present invention further includes any variant of the above process, in which an inter-mediate product obtainable at any stage thereof, e.g. a compound of formula (IIa), formula (IIb), formula (IIc), formula (IId), formula (IIe), formula (IIf), formula (IIg), formula (III), formula (IV), formula (V), formula (VI), formula (VII), formula (VIII), formula (IX) formula (X), formula (XI), formula (XII), formula (XIII), formula (XIV), formula (XV), formula (XVI), formula (XVII), formula (XVIII), formula (XIX), formula (XX), formula (XXI), formula (XXII), formula (XXIII) or formula (XXIV) is used as the starting material, and the remaining steps are carried out, or in which the reaction components are used in the form of their salts. Moreover, any of the alternative routes may be combined appropriately via common intermediates to yield the compounds of formula (A).

When required, protecting groups may be introduced to protect the functional groups present from undesired reactions with reaction components under the conditions used for carrying out a particular chemical transformation of the present invention. The need and choice of protecting groups for a particular reaction is known to those skilled in the art and depends on the nature of the functional group to be protected (amino, hydroxyl, thiol etc.), the structure and stability of the molecule of which the substituent is a part and the reaction conditions.

Well-known protecting groups that meet these conditions and their introduction and removal are described, for example, in McOmie, "*Protective Groups in Organic Chemistry*", Plenum Press, London, N.Y. (1973); Greene and Wuts, "*Protective Groups in Organic Synthesis*", John Wiley and Sons, Inc., NY (1999).

In the processes cited herein, activated derivatives of carboxylic acids of formula (VIIIa), include acid chlorides, bromides and fluorides, mixed anhydrides, lower alkyl esters and activated esters thereof. Mixed anhydrides are preferably such from pivalic acid, or lower alkyl hemiesters of carbonic acids, such as ethyl or isobutyl analogs. Activated esters include, for example, succinimido, phthalimido or 4-nitrophenyl esters. Carboxylic acids of formula (VII) can be converted to their activated derivatives using methods described herein or in the art.

The above-mentioned reactions are carried out according to standard methods, in the presence or absence of diluent, preferably such as are inert to the reagents and are solvents thereof, of catalysts, condensing or said other agents respectively and/or inert atmospheres, at low temperatures, room temperature or elevated temperatures (preferably at or near the boiling point of the solvents used), and at atmospheric or super-atmospheric pressure.

Suitable solvents are water and organic solvents, especially polar organic solvents, which can also be used as mixtures of at least two solvents. Examples of solvents are hydrocarbons (petroleum ether, pentane, hexane, cyclohexane, methylcyclohexane, benzene, toluene, xylene), halogenated hydrocarbon (dichloromethane, chloroform, tetrachloroethane, chlorobenzene); ether (diethyl ether, dibutyl ether, tetrahydrofuran, dioxane, ethylene glycol dimethyl or diethyl ether); carbonic esters and lactones (methyl acetate, ethyl acetate, methyl propionate, valerolactone); N,N-substituted carboxamides and lactams (dimethylformamide, dimethylacetamide, N-methylpyrrolidone); ketones (acetone, methylisobutylketone, cyclohexanone); sulfoxides and sulfones (dimethylsulfoxide, dimethylsulfone, tetramethylene sulfone); alcohols (methanol, ethanol, n- or i-propanol, n-, i- or t-butanol, pentanol, hexanol, cyclohexanol, cyclohexanediol, hydroxymethyl or dihydroxymethyl cyclohexane, benzyl alcohol, ethylene glycol, diethylene glycol, propanediol, butanediol, ethylene glycol monomethyl or monoethyl ether, and diethylene glycol monomethyl or monoethyl ether; nitriles (acetonitrile, propionitrile); tertiary amines (trimethylamine, triethylamine, tripropylamine and tributylamine, pyridine, N-methylpyrrolidine, N-methylpiperazine, N-methylmorpholine) and organic acids (acetic acid, formic acid).

The processes described herein above are preferably conducted under inert atmosphere, more preferably under nitrogen atmosphere.

Compounds of the present invention may be isolated using conventional methods known in the art, e.g., extraction, crystallization and filtration, and combinations thereof.

The following Examples are intended to illustrate the invention and are not to be construed as being limitations thereon. Temperatures are given in degrees Centrigrade. If not mentioned otherwise, all evaporations are performed under reduced pressure, preferably between about 5 and 50 mmHg (=20-133 mbar). The structure of final products, intermediates and starting materials is confirmed by standard analytical methods, e.g., microanalysis and spectroscopic characteristics, e.g., MS, IR and NMR. In general, abbreviations used are those conventional in the art.

EXAMPLE 1

Preparation of
(S)-5-hydroxymethyl-pyrrolidin-2-one

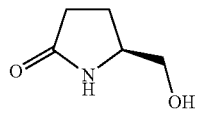

(IIa)

A suspension of 275 g of lithium borohydride in 15 L of anhydrous tetrahydrofuran is cooled to 10° C. and a solution of 1.6 kg of (S)-5-oxo-pyrrolidine-2-carboxylic acid methyl ester in 8 L of tetrahydrofuran is added within 2 hours. The resulting suspension is warmed to 40° C. and stirred for a further 3 hours. Water (1.8 L) is then added and the mixture filtered. The solid is then suspended in 7 L of tetrahydrofuran and heated to reflux for 75 minutes. After this time the mixture is cooled to 25° C. and filtered. The filtrate is treated slowly with 500 mL of a 1.0 M solution of oxalic acid in water at room temperature. The resulting suspension is filtered and the solid washed with 5 L of tetrahydrofuran. The solvent is then removed from the filtrate to provide an oil. The oil is re-dissolved in a mixture of 6.3 L of ethyl acetate and 0.7 L of ethanol at elevated temperature and the slightly cloudy solution filtered. The clear solution is cooled to −25° C. and the resulting suspension stirred for 2 hours. The solid is collected by filtration, washed with ethyl acetate and dried to give the title compound.

The starting material may be prepared as follows.

A suspension of 0.4 kg of Dowex-H$^+$ ion exchange resin in 30 L of methanol containing 2 kg of D-pyroglutamic acid is stirred at relfux temperature for 72 hours. The mixture is cooled to room temperature and a further 0.17 kg of Dowex-H resin and 30 L of methanol is added and the mixture heated to reflux. Methanol is removed by distillation under vacuum. The reaction mixture is then treated with a further 30 L of methanol and the distillation repeated. This is repeated a further twice. Finally the mixture is concentrated in vacuum to a volume of around 10 L filtered and the solid washed with 10 L of methanol. The filtrate and washings are combined and the methanol removed by distillation to give an oil. The pure methyl ester is isolated by fractional distillation at 120-132° C. and 0.70 mBar to give the required ester.

EXAMPLE 2

Preparation of
(3S,5S)-5-hydroxymethyl-3-isopropyl-pyrrolidone

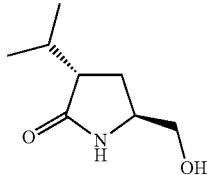

(IIIa)

A solution of 16.5 g of (3R,6S,7aS)-6-isopropyl-3-phenyltetrahydro-pyrrolo[1,2-c]oxazol-5-one in 175 mL of dichloromethane is treated with 15.35 g of trifluoroacetic acid at room temperature. The resulting solution is stirred for 24 hours at room temperature and a further 14 g of trifluoroacetic acid added. Stirring is continued for a further 24 hours and the solvent removed in vacuum. The residue is treated with 50 mL of water and 100 mL of dichloromethane and the pH of the two-phase mixture adjusted to 12 with concentrated sodium hydroxide solution. Solid sodium chloride is added and the mixture stirred. The organic layer is removed under reduced pressure to give (3S,5S)-5-hydroxymethyl-3-isopropyl-pyrrolidin-2-one as a semi-solid. mp. 55.9° C., $[\alpha]_D=+47.9°$ (1% in MeOH)

The starting material may be prepared as follows:

A suspension of 148.5 g of (S)-5-hydroxymethyl-pyrrolidin-2-one in 891 mL of toluene is treated with 172.1 mL of benzaldehyde at room temperature. p-Toluenesulphonic acid (2.94 g) is added and the reaction mixture stirred at reflux for 20 hours with azeotropic removal of water. The reaction mixture is treated with 500 mL of a 5% solution of sodium hydrogen carbonate in water. The organic layer is separated and washed once with 500 mL of a 40% solution of sodium bisulphite solution followed by 2×250 mL of water. The organic layer is dried with sodium sulphate, filtered and the solvent removed to give an oil. Fractional distillation in vacuum produces pure (3R,7aS)-3-phenyl-tetrahydro-pyrrolo[1,2-c]oxazol-5-one.

A suspension of 450 g of a 60% dispersion of sodium hydride in mineral oil in 3.3 L of tetrahydrofuran is warmed to 50° C. and treated with 1.8 kg of diethyl carbonate. A solution of 800 g (3R,7aS)-3-phenyl-tetrahydro-pyrrolo[1,2-c]oxazol-5-one in 1.6 L of tetrahydrofuran is added within 15 minutes and the resulting reaction mixture stirred at 55° C. for 180 minutes. At 55-60° C. a solution of 1.85 kg of isopropyl bromide in 1.8 kg of dimethyl formamide is added maintaining the temperature between 55-60° C. Finally the reaction mixture was warmed to reflux and stirred for 20 hours. The reaction mixture is cooled to room temperature and treated with 5 L of a 10% solution of citric acid in water. The reaction mixture is extracted twice with 3 L of ethyl acetate and the organic extracts combined. The organic layers are washed twice with brine and dried. Removal of the solvent gave 1.84 kg of an oil. The oil is chromatographed on silica-gel using hexane/ethyl acetate mixtures. The product containing fractions are combined and the solvent is removed to give the desired compound as an oil. Crystallisation from an ethyl acetate/hexane mixture delivers 730 g of (3R,6R,7aS)-6-isopropyl-5-oxo-3-phenyl-tetrahydro-pyrrolo[1,2-c]oxazole-6-carboxylic acid ethyl ester. A solution of 960 g of (3R,6R,7aS)-6-isopropyl-5-oxo-3-phenyl-tetrahydro-pyrrolo[1,2-c]oxazole-6-carboxylic acid ethyl ester in 8 L of tetrahydrofuran is treated with 3.33 L of a 2.0 M solution of sodium hydroxide at room temperature. The reaction mixture is stirred for 24 hours toluene (5.15 L) is added and the reaction pH adjusted to between 2-4 with a 10% solution of citric acid. The layers are separated and the aqueous layer saturated with sodium chloride. The aqueous layer is washed with 4 L of toluene and the organic layers combined and dried. The toluene solution is heated to reflux for 48 hours. Finally the solution is cooled to 70° C. and the toluene removed under a slight negative pressure to give (3R,6S,7aS)-6-isopropyl-3-phenyltetrahydro-pyrrolo[1,2-c]oxazol-5-one.

EXAMPLE 3

Preparation of (3S,5S)-5-tert-butoxycarbonyloxymethyl-3-isopropyl-2-oxo-pyrrolidine-1-carboxylic acid tert-butyl ester

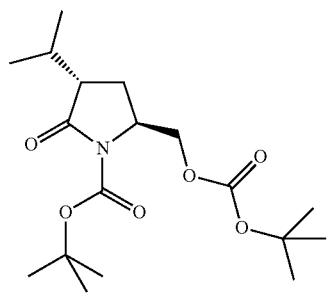
(IVa)

Route A:

A solution of 20.14 g of (3S,5S)-5-hydroxymethyl-3-isopropyl-pyrrolidin-2-one in 200 mL of tetrahydrofuran is treated with 39.36 g of di-tert-butyl dicarbonate, 17.23 g of triethylamine and 1.04 g of dimethylamino pyridine. The mixture is stirred at room temperature for 24 hours and warmed to 40° C. for 6 hours. The solvent is removed under reduced pressure and the residue treated with 60 mL of a 10% solution of citric acid and 200 mL of ethyl acetate. The organic layer is removed and the aqueous layer re-extracted with 200 mL of ethyl acetate. The combined organic layers are concentrated to a volume of around 40 mL and 50 mL of hexane is added. The thin suspension is cooled to 0° C. and stirred overnight. The crystalline solid is collected by filtration, washed and dried to give the title compound. X-ray single crystal! analysis of the compound confirms the absolute configuration on both stereo centers. mp.: 111-112° C., $[\alpha]_D = -60.3°$ (1% $CH_2Cl_2$).

$^1$H-NMR: 4.27-4.22 (2H, brm), 4.11-4.15 (1H, dd), 2.59-2.65 (1H, m), 2.16-2.21 (1H, brm), 1.88-1.93 (2H, brm), 1.50 (9H, s), 1.44 (9H, s), 0.96 (3H, d), 0.82 (3H, d).

Route B:

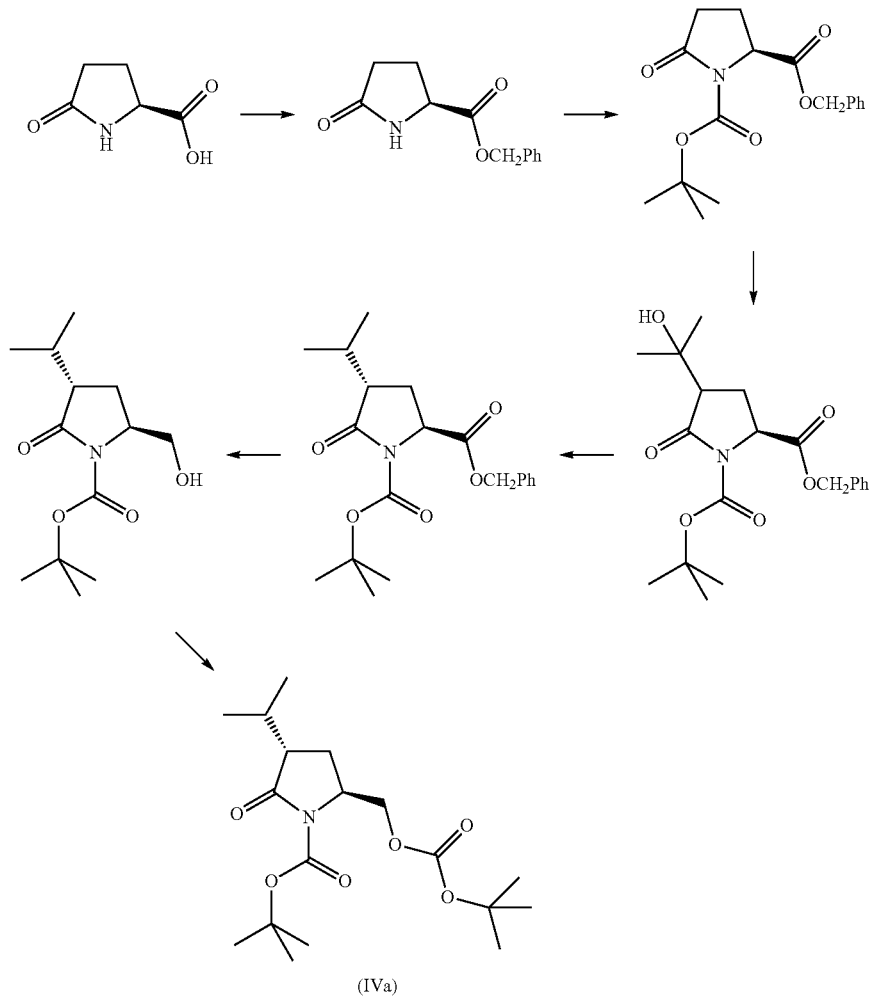
(IVa)

A solution of 12.8 g of (3S,5S)-5-hydroxymethyl-3-isopropyl-2-oxo-pyrrolidine-1-carboxylic acid tert-butyl ester in 100 mL of dichloromethane is treated with 0.5 g of dimethylamino pyridine is treated with 7.8 g di-tert-butyl dicarbonate at room temperature. The mixture is stirred for 4 hours at room temperature. The reaction mixture is then washed twice with 400 mL of 0.5 M sulphuric acid. The organic phase is separated and the solvent removed to give the title compound as a semi-crystalline solid.

The starting material is prepared as follows:

A solution of 387 g of L-pyro-glutamic acid in 300 mL of dimethylformamide is treated with 103.6 g of potassium carbonate at room temperature. Benzyl bromide (35.6 mL) is added and the suspension stirred room temperature for 4 hours. The suspension is filtered and the solid washed with 300 mL of acetone. The filtrate is evaporated at 50° C. to give an oil. The oil is dissolved in 300 mL of ethyl acetate and washed with 300 mL of water. The aqueous phase is re-extracted with 150 mL of ethyl acetate and the organic layers combined, dried and the solvent removed to give (S)-5-oxo-pyrrolidine-2-carboxylic acid benzyl ester as an oil.

To a solution of 78.9 g of (S)-5-oxo-pyrrolidine-2-carboxylic acid benzyl ester in 400 mL of dichloromethane is added 2.20 g of dimethylaminopyridine and 78.54 g of di-tert-butyl carbonate at room temperature. The mixture is stirred for 4 hours at room temperature. The reaction mixture is then washed twice with 400 mL of 0.5 M sulphuric acid. The organic phase is separated and the solvent removed to give (S)-5-oxo-pyrrolidine-1,2-dicarboxylic acid 2-benzyl ester 1-tert-butyl ester as a semi-crystalline solid.

A solution of lithium hexamethyldisilazide in tetrahydrofuran is cooled to −78° C. and treated with a solution of 15.95 g of (S)-5-oxo-pyrrolidine-1,2-dicarboxylic acid 2-benzyl ester 1-tert-butyl ester in 100 mL of tetrahydrofuran maintaining the temperature at −78° C. The resulting mixture was stirred for 40 minutes and a mixture of 40 mL of acetone and 7 mL of boron trifluoride diethyl etherate added within 20 minutes. The reaction mixture is stirred for 2.5 hours at −78° C. and 300 mL of a 10% solution of citric acid added and the reaction mixture warmed to room temperature. The layers are separated and the aqueous layer is re-extracted with 300 mL of dichloromethane. The combined organic layers are dried, filtered and the solvent removed to give (S)-4-(1-hydroxy-1-methyl-ethyl)-5-oxo-pyrrolidine-1,2-dicarboxylic acid 2-benzylester 1-tert-butyl ester as an oil.

A solution of 75.8 g of (S)-4-(1-hydroxy-1-methyl-ethyl)-5-oxo-pyrrolidine-1,2-dicarboxylic acid 2-benzylester 1-tert-butyl ester in 200 mL of tetrahydrofuran is treated with 41.8 g of triethylamine and 1.2 g of dimethylamino pyridine and cooled to 0° C. Oxalic acid methyl ester chloride (31.7 mL) is added dropwise within 60 minutes. The reaction mixture is stirred for 24 hours at room temperature and 200 mL of tert-butyl methyl ether and 200 mL of water is added. The organic layer is separated and washed with 100 mL of saturated sodium bicarbonate solution followed by 100 mL of water. The organic phase is dried and the solvent removed to give 87.9 g of the intermediate oxalic acid ester as an oil. This oil is re-dissolved in 350 mL of toluene and treated sequentially with 0.6 g of azobisisobutyronitrile and 100.7 mL of tri-n-butyl tin hydride. The mixture is heated to reflux for 60 minutes and a further 0.6 g portion of azobisisobutyronitrile is added. This is continued for a total of 4 hours (5 additions). The reaction mixture is concentrated in vacuum to give an oil. The oil is re-dissolved in 300 mL of acetonitrile and washed 4 times with 400 mL of hexane. The acetonitrile phase is concentrated in vacuum to give an oil. Chromatography on silica-gel with ethyl acetate/hexane mixtures, combination of the product containing fractions and removal of the solvent gives (2S,4S)-4-isopropyl-5-oxo-pyrrolidine-1,2-dicarboxylic acid -2-benzyl ester-1-tert-butyl ester.

A suspension of 27 g of lithium borohydride in 15 mL of anhydrous tetrahydrofuran is cooled to 10° C. and a solution of 15.4 g of (2S,4S)-4-isopropyl-5-oxo-pyrrolidine-1,2-dicarboxylic acid -2-benzyl ester-1-tert-butyl ester in 80 mL of tetrahydrofuran is added within 2 hours. The resulting suspension is warmed to 40° C. and stirred for a further 3 hours. Water (800 mL) is then added and the mixture filtered. The solid is then suspended in 700 mL of tetrahydrofuran and heated to reflux for 75 minutes. After this time the mixture is cooled to 25° C. and filtered. The filtrate is treated slowly with 500 mL of a 1.0 M solution of oxalic acid in water at room temperature. The resulting suspension is filtered and the solid washed with 500 mL of tetrahydrofuran. The solvent is then removed from the filtrate to provide an oil. The oil is re-dissolved in a mixture of 630 mL of ethyl acetate and 0.07 L of ethanol at elevated temperature and the slightly cloudy solution filtered. The clear solution is cooled to −25° C. and the resulting suspension stirred for 2 hours. The solid is collected by filtration, washed with ethyl acetate and dried to give (3S,5S)-5-hydroxymethyl-3-isopropyl-2-oxo-pyrrolidine-1-carboxylic acid tert-butyl ester.

EXAMPLE 4

Preparation of Carbonic Acid (2S,4S)-2-tert-butyl-carbonylamino-4-[4-methoxy-3-(3-methoxy-propoxy)-benzoyl]-5-methyl-hexylester tert-butyl ester (Va)

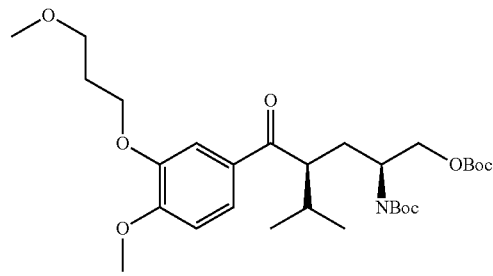

A solution of 7.9 g of 4-bromo-1-methoxy-2-(3-methoxypropoxy)-benzene in 125 mL of tetrahydrofuran is cooled to −78° C. A solution of n-butyllithium (14.219 g of a 1.6 M solution in hexane) is added within 50 minutes. The reaction mixture is stirred for 90 minutes at −78° C. and treated slowly with 75 mL of a tetrahydrofuran solution of 8.93 g of (3S, 5S)-5-tert-butoxycarbonyloxymethyl-3-isopropyl-2-oxo-pyrrolidine-1-carboxylic acid tert-butyl ester. The resulting reaction mixture is stirred for 3 hours at −78° C. Finally the temperature is raised to −40° C. and the mixture stirred for 45 minutes. Acetic acid (4 mL) was added and the solvent removed by evaporation. The residue is dissolved in 100 mL of ethyl acetate and washed with two 75 mL portions of saturated sodium bicarbonate solution followed by one portion of 150 mL of water. The organic phase was dried and the solvent removed to give an oil. Chromatography on silica-gel, eluting with hexane/ethyl acetate gives, after combination of the product containing fractions and removal of the solvent, affords the title compound as an oil.

$^1$H-NMR (CDCl$_3$) 7.50(2H, m), 6.81(1H, m), 4.60(1H, d), 4.15(2H, t), 4.05(2H, m), 3.90(3H, s), 3.55(2H, t), 3.40(1H, m), 3.35(3H, s), 2.15(2H, m), 2.05(1H, m), 1.60(1H, m), 1.45(9H, s), 1.40-1.20(9H, Brs), 1.00(3H, d), 0.90(3H, d).

EXAMPLE 5

Preparation of Carbonic Acid (2S,4S)-2-tert-butyl-carbonylamino-4-[4-methoxy-3-(3-methoxy-propoxy)-benzyl]-5-methyl-hexylester tert-butyl ester

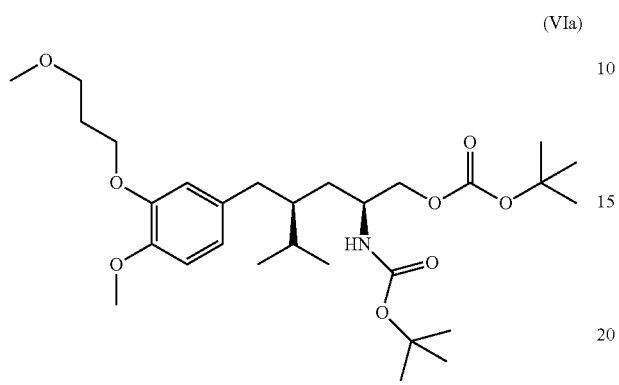

(VIa)

Carbonic acid (2S,4S)-2-tert-butylcarbonylamino-4-[4-methoxy-3-(3-methoxy-propoxy)-benzoyl]-5-methyl-hexylester tert-butyl ester (2.67 g) is dissolved in 25 mL of a mixture of ethanol/acetic acid, 2/1 at room temperature. Palladium metal, 10% on charcoal (0.3 g) is added and the suspension placed under an atmosphere of hydrogen at a pressure of 5 bar. Hydrogenation is continued for 3 days at 50° C. with periodic addition of more catalyst. The reaction mixture is filtered and the solvent removed to give an oil. The oil is purified by chromatography on silica-gel eluting with hexane/ethyl acetate mixtures. The product fractions are combined and the solvent is removed to give the title compound as an oil.

EXAMPLE 6

Preparation of {(1S,3S)-1-hydroxymethyl-3-[4-methoxy-3-(3-methoxypropoxy)-benzyl]-4-methyl-pentyl}-carbamic acid tert-butyl ester

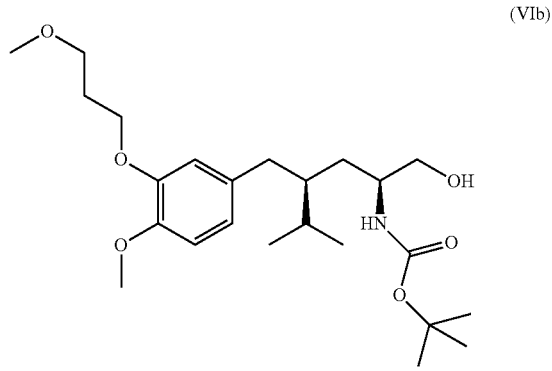

(VIb)

Regioselective hydrolysis is carried out according to a literature procedure, e.g. as described in J. Amer. Chem. Soc., 2000, 122, 10708.

EXAMPLE 7

Preparation of (2S,4S)-2-tert-butoxycarbonylamino-4-[4-methoxy-3-(3-methoxy-propoxy)-benzyl]-5-methylhexanoic acid

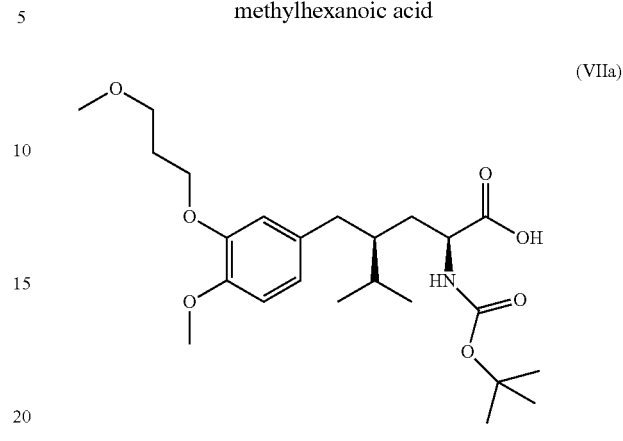

(VIIa)

To a solution of 4.39 g {(1S,3S)-1-hydroxymethyl-3-[4-methoxy-3-(3-methoxypropoxy)-benzyl]-4-methylpentyl}-carbamic acid tert-butyl ester in 50 mL of dichloromethane is cooled to 0° C. and treated with TEMPO (0.2 g), 25 mL of a 2.75 M solution of potassium bromide and 15 mL of a 1.6 M solution of potassium hydrogen carbonate solution. The rapidly stirred two-phase system is treated with bleach (15 mL of a 11% solution) and the mixture stirred for 60 minutes at 0° C. A 1.0 M solution of sodium thiosulphate is added and the mixture stirred for 15 minutes at room temperature. The organic layer is then separated and washed twice with 100 mL of water. The solvent is removed to provide the intermediate alcohol as an oil which is used directly for the next step. The oil is dissolved in 20 mL of tert-butanol and 5 mL of 2-methyl-2-butene is added. A solution of sodium chlorite (1.2 g, of a 80% solution) and sodium dihydrogen phosphate (10.03 g) in 20 mL of water is added dropwise over 15 minutes. The reaction mixture is stirred for 3 hours at room temperature. The mixture is then diluted with brine and extracted three times with 50 mL of dichloromethane. The combined organic layers are dried and the solvent is removed to give the title compound as an oil.

EXAMPLE 8

Preparation of (2S,5S,7S)-5-tert-butoxycarbonylamino-3-ethoxycarbonyl-2-isopropyl-7-[4-methoxy-3-(3-methoxypropoxy)-benzyl]-8-methyl-4-oxo-3-propoxycarbonyl-nonanoic acid ethyl ester

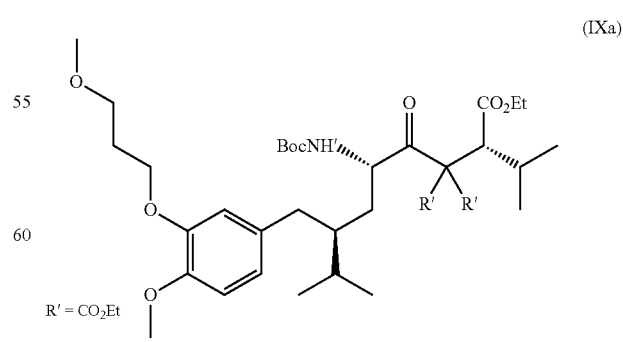

(IXa)

A solution of 4.53 g of (2S,4S)-2-tert-butoxycarbonylamino-4-[4-methoxy-3-(3-methoxypropoxy)-benzyl]-5- methylhexanoic acid in 25 mL of toluene is heated to reflux and oxalyl chloride (1.75 g) is added. The mixture is then stirred at room temperature. The solvent is then removed in vacuum and a further 25 mL of toluene added. Distillation is repeated and a further 25 mL of toluene added. Distillation is repeated to give the acid chloride as an oil. This oil is re-dissolved in tetrahydrofuran and cooled to 0° C. and added to a solution of 11 mmol of the sodium salt of (R)-2-(bis-ethoxy-carbonylmethyl)-3-methylbutyric acid ethyl ester in tetrahydrofuran (prepared by treatment of (R)-2-(bis-ethoxycarbonyl-methyl)-3-methylbutyric acid ethyl ester with sodium hydride). The mixture is stirred for 2 hours at room temperature and 20 mL of a 10% solution of citric acid is added. The organic layer is separated, dried and the solvent removed in vacuum to produce the title compound as a semi crystalline solid.

EXAMPLE 9

Preparation of (2S,5S,7S)-5-tert-butoxycarbony-lamino-2-isopropyl-7-[4-methoxy-3-(3-methoxypropoxy)-benzyl]-8-methyl-4-oxo-nonanoic acid

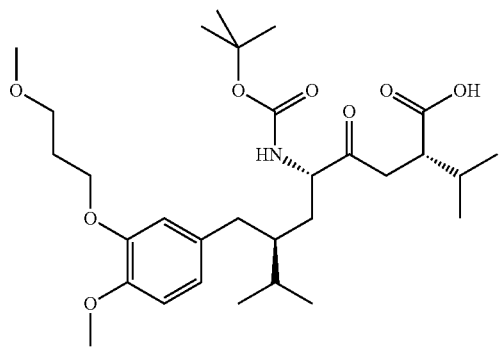

(Xa)

A solution of 10.0 g of (2S,5S,7S)-5-tert-butoxycarbony-lamino-3-ethoxycarbonyl-2-isopropyl-7-[4-methoxy-3-(3-methoxypropoxy)-benzyl]-8-methyl-4-oxo-3-propoxycar-bonyl-nonanoic acid ethyl ester in 20 mL of ethanol is treated with 25 mL of a 37% solution of sodium hydroxide at room temperature. The reaction mixture is stirred for 24 hours at room temperature and the ethanol removed by distillation in vacuum. The residue is extracted twice with 25 mL of dichloromethane. The pH of the aqueous layer is carefully adjusted to 2.5 with 2 N hydrochloric acid at 0° C., the reaction mixture is then stirred for 16 hours and extracted 4 times with 50 mL of dichloromethane. The organic layer is dried and the solvent removed to give the title compound as an oil.

EXAMPLE 10

Preparation of {(1S,3S)-1-((2S,4S)-4-isopropyl-5-oxo-tetrahydrofuran-2-yl)-3-[4-methoxy-3-(3-methoxypropoxy)-benzyl]-4-methyl-pentyly}-carbamic acid tert-butyl ester

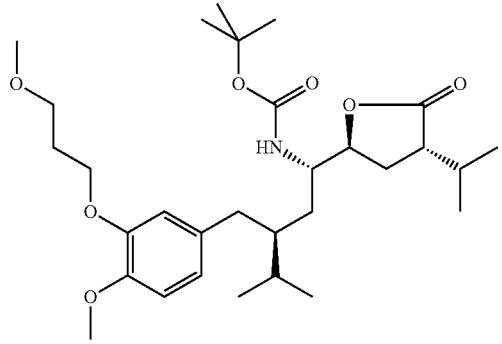

(XIa)

A solution of 5.51 g of (2S,5S,7S)-5-tert-butoxycarbony-lamino-2-isopropyl-7-[4-methoxy-3-(3-methoxypropoxy)-benzyl]-8-methyl-4-oxo-nonanoic acid in 25 mL of tetrahydrofuran is cooled to −30° C. and 10 mL of a 1.0 M solution of K-selectride in tetrahydrofuran is added dropwise within 30 minutes. The mixture is stirred for 2 hours at 30° C. and warmed to 0° C. and stirred for 16 hours. The reaction mixture is quenched with 50 mL of 1.0 M hydrochloric acid and extracted three times with 100 mL of dichloromethane. The organic layer is dried and the solvent is removed to give the title compound as a semi solid.

EXAMPLE 11

Preparation of aliskiren via ((1S,2S,4S)-4-(2-car-bamoyl-2-methylpropyl-carbamoyl)-2-hydroxy-1-{(S)-2-[4-methoxy-3-(3-methoxypropoxy)-benzyl]-3-methylbutyl}-5-methylhexyl)-carbamic acid tert-butyl ester

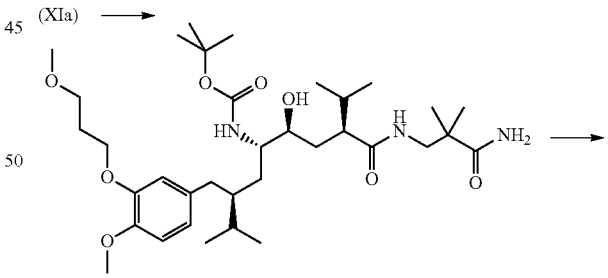

(XIb)    aliskiren

Route A:

A solution of compound (XIa), 3-amino-2,2-dimethylpro-pionamide and 2-hydroxypyridine in tert-butylmethyl ether containing triethylamine is stirred for 18 hours at 83° C. The reaction mixture is then cooled to room temperature and diluted with toluene and washed with 10% aqueous sodium hydrogen sulphate solution. The organic phase is separated and washed with water, and the solvent is removed in vacuum to give an oil. This oil is suspended in hexane and stirred. The solid is removed by filtration and the hexane removed in vacuum to give ((1S,2S,4S)-4-(2-carbamoyl-2-methylpropylcarbamoyl)-2-hydroxy-1-{(S)-2-[4-methoxy-3-(3-methoxypropoxy)-benzyl]-3-methylbutyl}-5-methylhexylycarbamic acid tert-butyl ester, compound (XIb), as a foam.

Compound of formula (XIb) is dissolved in a solution of trifluoroacetic acid in methylene chloride at room temperature. The reaction mixture is stirred for 2 hours and the pH adjusted to 10 with 37% sodium hydroxide solution. The aqueous phase is extracted three times with 100 mL of dichloromethane. (for characterization see e.g. EP 0 678 503, Example 137).

From the free compound or the hydrochloride salt obtainable, for example the hemifumarate salt of the title compound can be prepared, for example as described in U.S. Pat. No. 6,730,798, example J1 (comprising mixing with fumaric acid, dissolution in ethanol, filtration, evaporation of the obtained solution, re-dissolving of the residue in acetonitrile, inoculation with a small amount of the title compound's hemifumarate salt and isolation of the precipitating material), incorporated by reference herein especially with regard to this salt formation reaction.

Route B: From compound of formula (Xa) via ((1S,2S)-4-(2-carbamoyl-2-methylpropylcarbamoyl)-1-{(S)-2-[4-methoxy-3-(3-methoxypropoxy)-benzyl]-5-methyl-2-oxohexyl)-carbamic acid tert-butyl ester

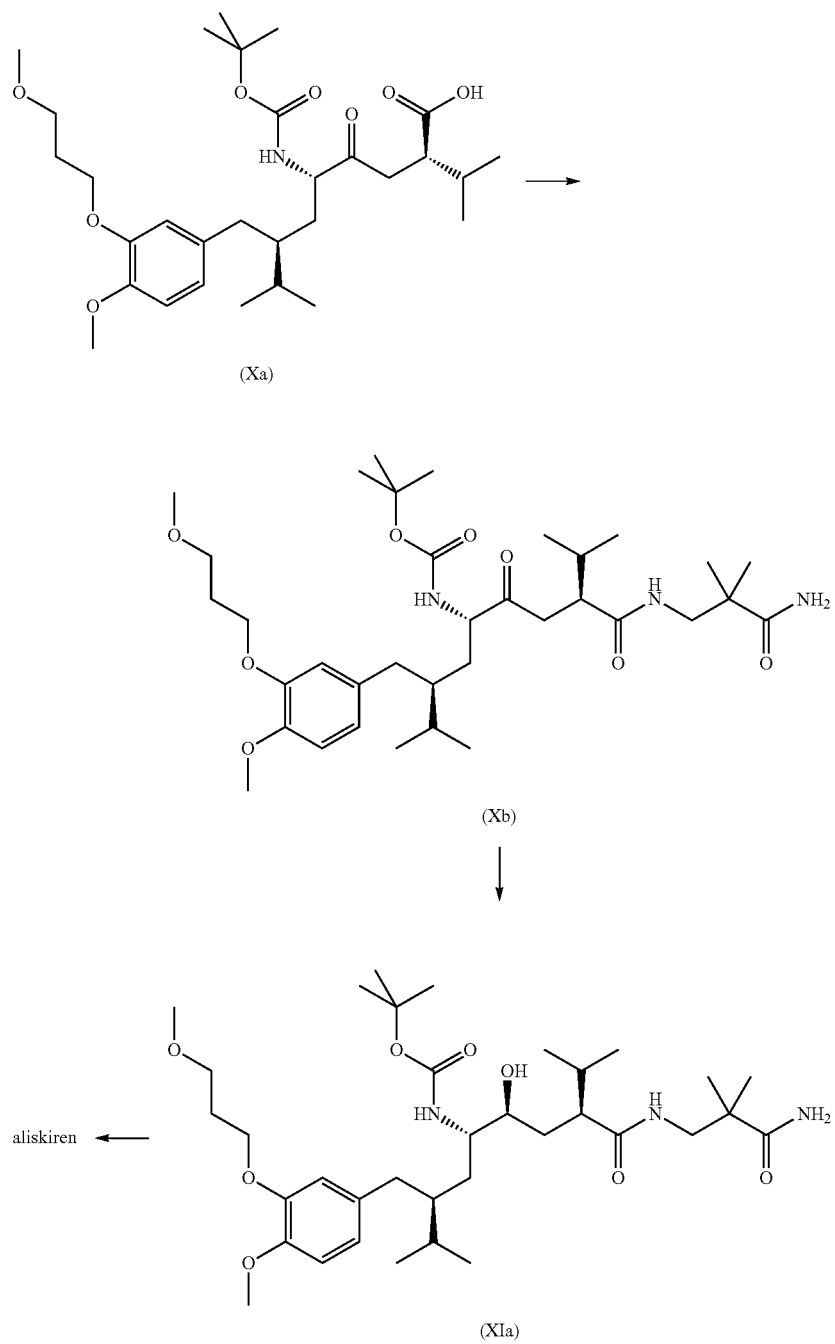

Compound of formula (Xa) is converted to the amide (Xb) by standard peptide coupling methods. Reduction as above.). Experimental details can be found in Houben-Weyl, Methoden der Organische Chemie, 4$^{th}$ Ed, Synthese von Peptiden 1.

Alternative Route to Compounds of Formula (XI) as Outlined in Scheme 4

Step A0) {(1S,3S)-1-Formyl-3-[4-methoxy-3-(3-methoxy-propoxy)-benzyl]-4-methyl-pentyl}-carbamic acid tert-butyl ester (XIVa)

The N-Boc-protected alcohol (VIa) is selectively oxidized to the corresponding aldehyde (XIVa) using the following literature methods: a) F. Montanari et al., J.O.C., 54, 2970 (1989) or b) Review: H. van Bekkum et al., Synthesis 1153 (1996).

Step A) 4S,5S,7S)-5-tert-Butoxycarbonylamino-4-hydroxy-7-[4-methoxy-3-(3-methoxy-propoxy)-benzyl]-8-methyl-non-2-ynoic acid ethyl ester (XVa)

B) (4S,5S,7S)-5-tert-Butoxycarbonylamino-4-hydroxy-7-[4-methoxy-3-(3-methoxy-propoxy)-benzyl]-8-methyl-nonanoic acid ethyl ester (XVIa)

dissolved in methylene chloride and the resulting solution was washed twice with 200 mL of water. The aqueous phases are re-extracted with a further 200 mL of methylene chloride and the organic phases are combined and the solvent removed. The residue is re-dissolved in ethyl acetate and filtered through a bed of silica gel eluting with ethyl acetate. The product containing fractions are combined and the solvent removed in vacuum to give 31.4 g of the acetylenic alcohol as a red oil.

$^1$H-NMR (CDCl$_3$): 6.8-6.65 (3H, m, Ph), 4.71(1H, Brd, OH), 4.42(1H, Brd, CHNH), 4.30-4.05(4H, m, 2×CH$_2$), 3.81 (3H, s, MeO), 3.70(1H,m, CHOH), 3.57(2H, m, CH$_2$O), 3.35 (3H, s, MeO), 2.50(1.5H, m, CHPh and part of a CH signal), 2.10(2.5H, CH$_2$ and part of a CH signal), 1.80-1.20(16H, m), 1.85(6H, d, iPr).

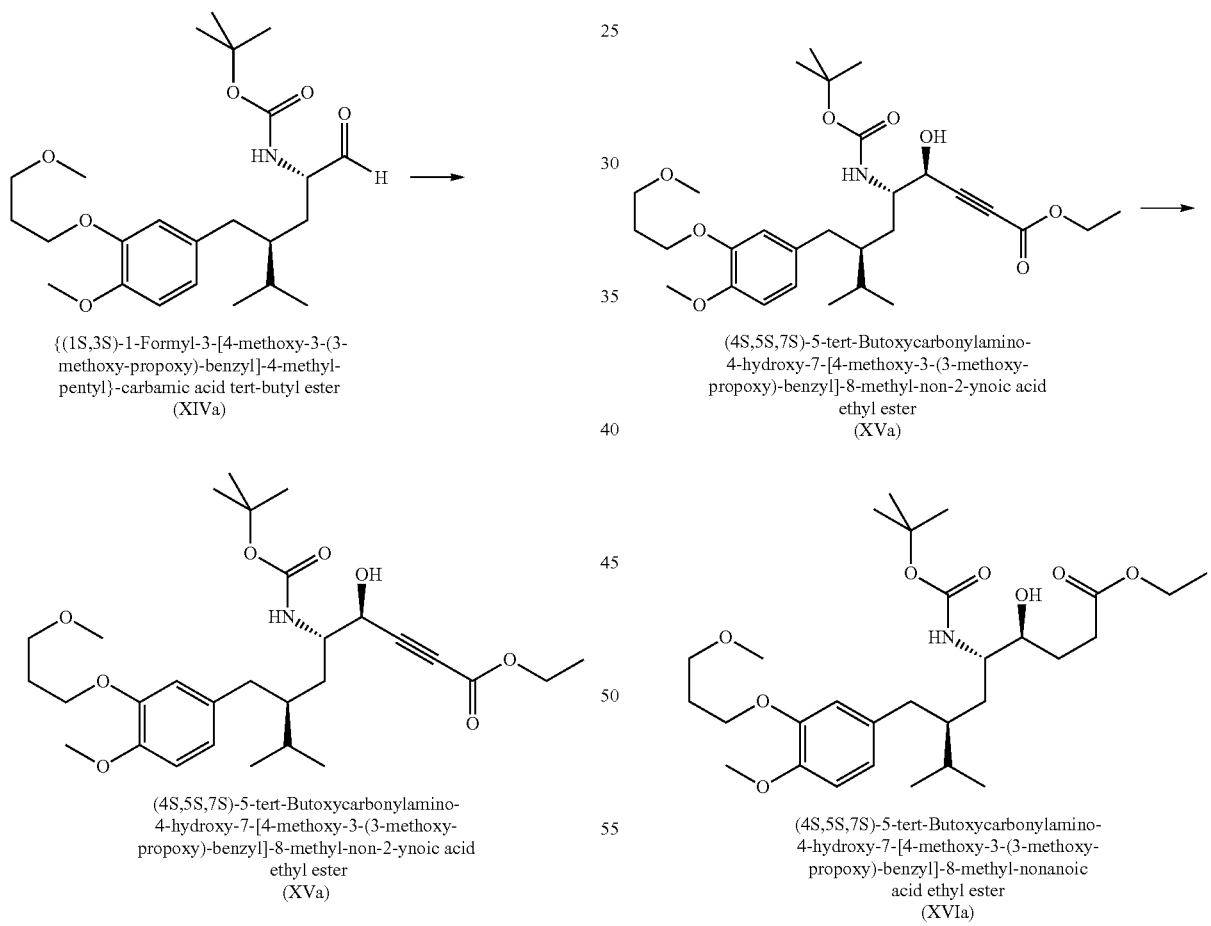

{(1S,3S)-1-Formyl-3-[4-methoxy-3-(3-methoxy-propoxy)-benzyl]-4-methyl-pentyl}-carbamic acid tert-butyl ester
(XIVa)

(4S,5S,7S)-5-tert-Butoxycarbonylamino-4-hydroxy-7-[4-methoxy-3-(3-methoxy-propoxy)-benzyl]-8-methyl-non-2-ynoic acid ethyl ester
(XVa)

(4S,5S,7S)-5-tert-Butoxycarbonylamino-4-hydroxy-7-[4-methoxy-3-(3-methoxy-propoxy)-benzyl]-8-methyl-non-2-ynoic acid ethyl ester
(XVa)

(4S,5S,7S)-5-tert-Butoxycarbonylamino-4-hydroxy-7-[4-methoxy-3-(3-methoxy-propoxy)-benzyl]-8-methyl-nonanoic acid ethyl ester
(XVIa)

To a 110 mL of a tetrahydrofuran solution of the lithium salt of propiolic acid ethyl ester (prepared by treating ethyl propiolate [12.27 g] with a molar equivalent of LDA and stirred for 30 minutes to ensure complete conversion) at −78° C. is added slowly a solution of the aldehyde (31 g, 70.8 mmol) in 60 mL of tetrahydrofuran. The reaction mixture is stirred for a further 60 minutes and quenched by slow addition of glacial acetic acid. The solvent is removed and the residue To a solution of the acetylene (14 g) in 350 mL of tetrahydrofuran is added platinum oxide (1.7 g). The resulting suspension is placed under an atmosphere of hydrogen and stirred for 2 hours 20 minutes at normal pressure. The suspension is filtered and the solvent removed to give 31 g of a colourless oil which is used without further purification in the next step (below).

C) [(1S,3S)-3-[4-Methoxy-3-(3-methoxy-propoxy)-benzyl]-4-methyl-1-((S)-5-oxo-tetrahydro-furan-2-yl)-pentyl]-carbamic acid tert-butyl ester (XVIIa)

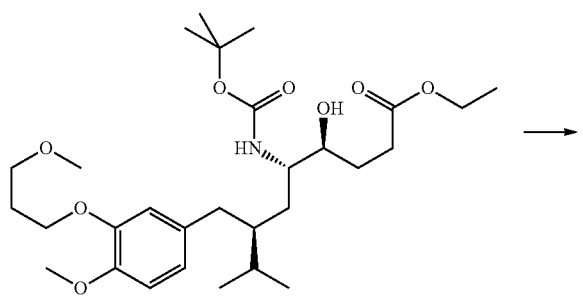

(4S,5S,7S)-5-tert-Butoxycarbonylamino-4-hydroxy-7-[4-methoxy-3-(3-methoxy-propoxy)-benzyl]-8-methyl-nonanoic acid ethyl ester
(XVIa)

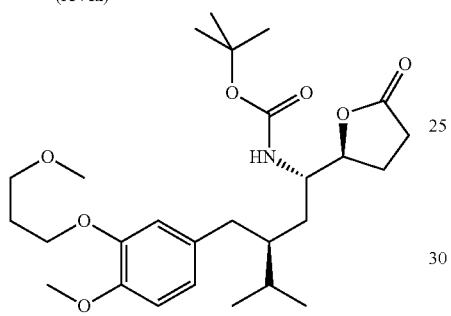

[(1S,3S)-3-[4-Methoxy-3-(3-methoxy-propoxy)-benzyl]-4-methyl-1-((S)-5-oxo-tetrahydro-furan-2-yl)-pentyl]-carbamic acid tert-butyl ester
(XVIIa)

The hydrogenation product from above (31 g) is dissolved in 50 mL of toluene and glacial acetic acid (16 mL) is added. The mixture is heated between 95-100° C. for 2 hours. The reaction mixture is cooled and the solvent is removed in vacuum. The residue is dissolved in 200 mL of toluene and diluted with 100 mL of water and 100 mL of saturated aqueous sodium bicarbonate. The mixture is extracted and the organic phase separated. The organic phase is re-washed with 100 mL of water. The aqueous phase is separated and combined with the previous water phases. The combined aqueous phases are re-extracted with a further 200 mL of toluene and the organic phase separated and combined with the previous organic phases. The solvent is removed in vacuum to give 27.4 g of a yellow oil. The residue is triturated with 100 mL of isopropanol upon which the product began to crystallise. Hexane (200 mL) is added slowly and the resulting suspension stirred at room temperature for 1 hour. The suspension is filtered and the product washed with hexane and dried in vacuum to give 14 g of the lactone as a white crystalline solid.

mp. 110° C., $[\alpha]_D$=−10.8° (1% in MeOH)

$^1$HNMR (DMSO, 120° C.) 6.85-6.79(2H, m, Ph), 6.70(1H, m, Ph), 6.25(1H, Brd, NH), 4.40(1H, m, lactone CH), 4.02 (2H, t, CH$_2$O), 3.75(3H, s, MeO), 3.62(1H, m, CHN), 3.30 (2H, t, CH$_2$O), 3.25(3H, s, MeO), 2.60-2.30(4H, m, CH$_2$CO -lactone and PhCH$_2$), 2.15(1H, m, CH lactone), 1.95-1.80 (3H, m, CH$_2$+CH lactone), 1.65(2H, m, 2×CH), 1.50(1H, m, CH), 1.40(9H, s, tBu), 1.20(1H, m, CH), 1.80(6H, d, 2×iPr).

D) (S)-5-{(1S,3S)-1-Amino-3-[4-methoxy-3-(3-methoxy-propoxy)-benzyl]-4-methyl-pentyl}-dihydro-furan-2-one (XVIIIa)

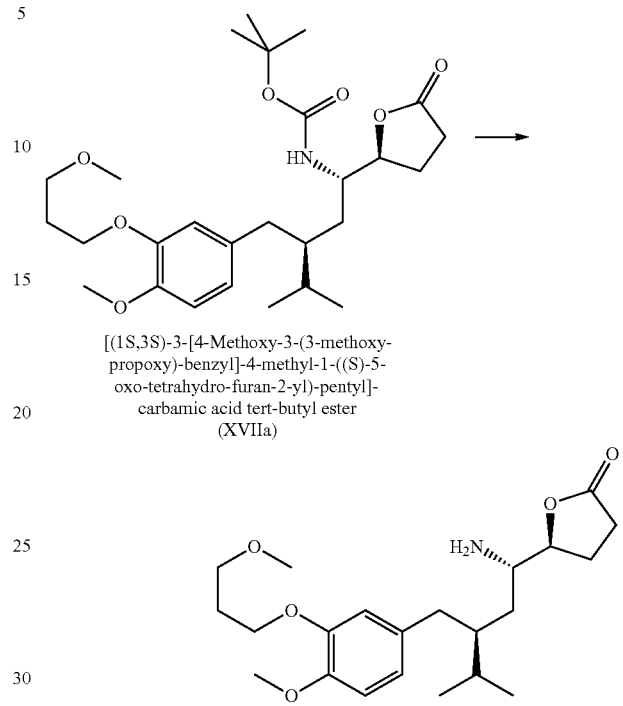

(S)-5-{(1S,3S)-1-Amino-3-[4-methoxy-3-(3-methoxy-propoxy)-benzyl]-4-methyl-pentyl}-dihydro-furan-2-one
(XVIIIa)

Lactone as HCl Salt:

A solution of 2.96 g of the lactone from above is dissolved in 10 mL of ethyl acetate and treated with a 1.55 M solution of hydrogen chloride gas in ethyl acetate. The mixture is stirred at room temperature for 3 hours. The solvent is removed in vacuum and the residue re-dissolved in 16 mL of a 1.55 M solution of hydrogen chloride gas in ethyl acetate and stirred at room temperature for a further 16 hours. The solvent is removed in vacuum to give 2.5 g of the amine hydrochloride as a yellow foam.

E) (5S,6S)-5-Hydroxy-6-{(S)-2-[4-methoxy-3-(3-methoxy-propoxy)-benzyl]-3-methyl-butyl}-piperidin-2-ane (XIXa)

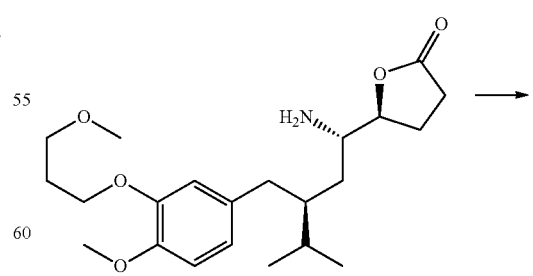

(S)-5-{(1S,3S)-1-Amino-3-[4-methoxy-3-(3-methoxy-propoxy)-benzyl]-4-methyl-pentyl}-dihydro-furan-2-one
(XVIIIa)

-continued

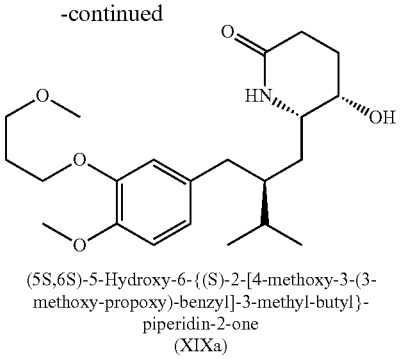

(5S,6S)-5-Hydroxy-6-{(S)-2-[4-methoxy-3-(3-methoxy-propoxy)-benzyl]-3-methyl-butyl}-piperidin-2-one
(XIXa)

The amine from above (13.0 g) is dissolved in 40 mL of methanol and 5.69 g of triethylamine is added at room temperature. The reaction mixture is stirred for 24 hours at room temperature and the solvent is removed in vacuum. The residue is re-dissolved in 100 mL of methylene chloride and the solution washed with 100 mL of water. The organic phase is dried over sodium sulphate and the solvent removed in vacuum to give 12.08 g of the piperidine-2-one as a yellow foam which is processed further without purification. $^1$HNMR (CDCl$_3$) 7.29(1H, Brs, NH), 6.85-6.65(3H, m, Ph), 5.45(1H, Brs, OH), 4.10(2H, t, CH$_2$O), 3.83(4H, m, MeO+CHOH), 3.58(2H, t, CH$_2$O), 3.35(3H, s, MeO), 3.22(1H, Brm, CHNH), 2.71-1.25(12H, m), 0.90(6H, m, 2×iPr).

F) (2S,3S)-3-tert-Butoxycarbonyloxy-2-{(S)-2-[4-methoxy-3-(3-methoxy-propoxy)-benzyl]-3-methyl-butyl}-6-oxo-piperidine-1-carboxylic acid tert-butyl ester (XXa)

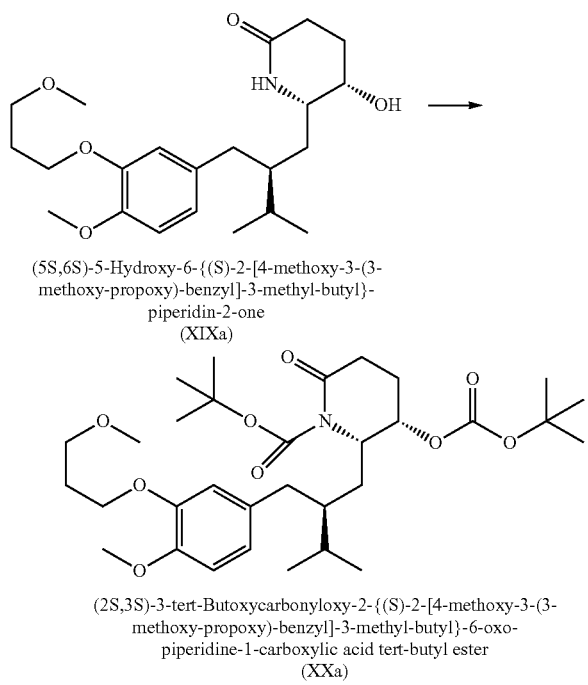

The piperidine-2-one from above (12.08 g) is dissolved in 20 mL of tetrahydrofuran at room temperature. N,N-dimethylaminopyridine (0.63 g), and triethylamine (5.98 g) are added followed by the addition of 12.89 g of di-tert. butyldicarbonate. The reaction mixture is stirred for 24 hours at room temperature and the solvent is removed in vacuum. The residue is dissolved in 150 mL of ethyl acetate and washed with 100 mL of a 5% aqueous solution of citric acid. The aqueous phase is re-extracted with 100 mL of ethyl acetate and the combined organic phases washed with 2×100 mL of water. The solvent is removed in vacuum to give 16.95 g of a yellow oil. Chromatography on silica-gel eluting with a toluene/ethyl acetate (1/1) mixture provided the pure bis-boc derivative which crystallizes on standing at room temperature. Mp. 89-90° C., after recrystallisation from EtOAc/c-hexane. [α]$_D$=13.0° (1% in MeOH).
$^1$HNMR (CDCl$_3$) 6.85-6.70(3H, m, Ph), 4.93(1H, m, CHOBoc), 4.70(1H, m, CHNHBoc), 4.11(2H, t, CH$_2$O), 3.83 (3H, s, MeO), 3.58(2H, t, CH$_2$O), 3.37(3H, s, MeO), 2.65-2.30(3H, m), 2.18-1.40(6H, m), 1.52(9H, s, tBu), 1.48(9H, s, tBu), 0.82(6H, m, 2×iPr).

G) (2S,3S)-3-tert-Butoxycarbonyloxy-5-(1-hydroxy-1-methyl-ethyl)-2-{(S)-2-[4-methoxy-3-(3-methoxy-propoxy)-benzyl]-3-methyl-butyl}-6-oxo-piperidine-1-carboxylic acid tert-butyl ester (XXIa)

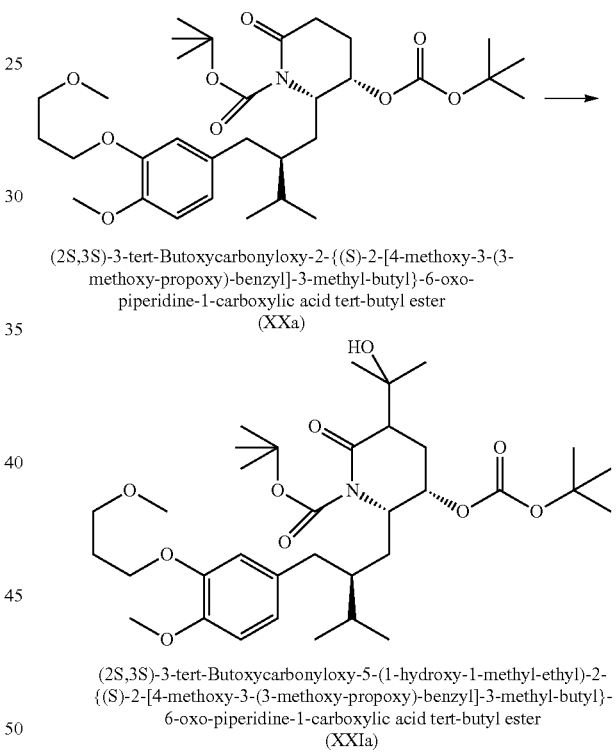

A solution of the bis-Boc derivative (2.46 g) in 10 mL of tetrahydrofuran is cooled to −78° C. and a solution of lithium hexamethyldisilazide (5.19 g) in 3 mL of tetrahydrofuran is added dropwise within 10 minutes. The resulting solution is stirred for 2 hours at −78° C. Boron trifluoride diethyletherate (0.705 g) is added followed by 1.93 g of acetone dissolved in 3 mL of tetrahydrofuran. The mixture is stirred for 1 hour at −78° C. and a further 0.12 g of boron trifluoride diethyletherate is added and stirring is continued for 24 hours at −78° C. After this time 100 mL of a pH7.0 buffer solution was added rapidly whereby the temperature rose to 0° C. The mixture is diluted with a further 60 mL of the pH 7.0 buffer solution and 200 mL of ethyl acetate. The aqueous phase is extracted and the organic phase separated. The aqueous phase is re-extracted with 100 mL of ethyl acetate and the organic phase separated. The organic phases are combined and the solvent removed in vacuum. The residue crystallised. The solid is suspended in 25 mL of hexane and stirred overnight at 0° C. Filtration of the solid and washing with hexane provided 2.37 g of the desired compound.

Mp. 118-119° C., after recrystallisation from EtOAc/hexane. [α]$_D$=34.8° (1% in MeOH).

$^1$HNMR (CDCl$_3$) 6.80-6.65(3H, m, Ph), 4.95-4.80(2H, m, OH+CHOBoc), 4.50(1H, m, CHNHBoc), 4.11(2H, t, CH$_2$O), 3.83(3H, s, MeO), 3.56(2H, t, CH$_2$O), 3.35(3H, s, MeO), 2.70-2.38(3H, m), 2.20-1.60(6H, m), 1.52(9H, s, tBu), 1.45(9H, s, tBu), 1.25(3H, s, Me), 1.18(3H, s, Me), 0.85(6H, m, 2×iPr).

H) (2S,3S)-3-tert-Butoxycarbonyloxy-5-isopropenyl-2-{(S)-2-[4-methoxy-3-(3-methoxy-propoxy)-benzyl]-3-methyl-butyl}-6-oxo-piperidine-1-carboxylic acid tert-butyl ester (XXIIa)

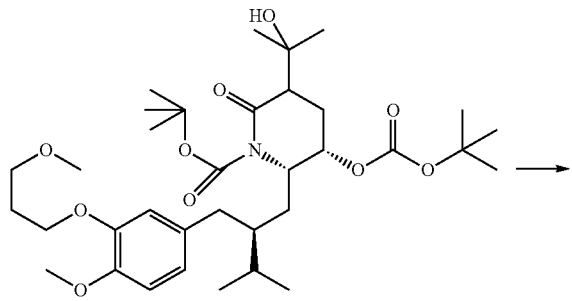

(2S,3S)-3-tert-Butoxycarbonyloxy-5-(1-hydroxy-1-methyl-ethyl)-2-{(S)-2-[4-methoxy-3-(3-methoxy-propoxy)-benzyl]-3-methyl-butyl}-6-oxo-piperidine-1-carboxylic acid tert-butyl ester (XXIa)

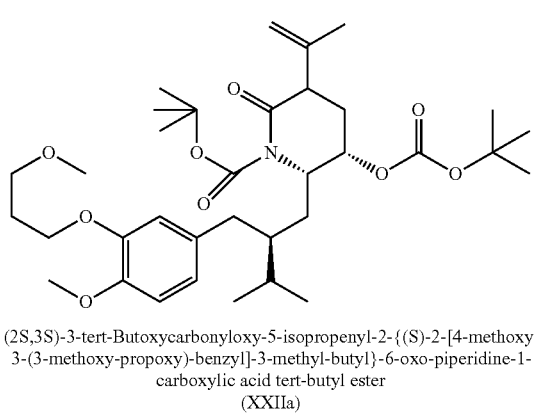

(2S,3S)-3-tert-Butoxycarbonyloxy-5-isopropenyl-2-{(S)-2-[4-methoxy-3-(3-methoxy-propoxy)-benzyl]-3-methyl-butyl}-6-oxo-piperidine-1-carboxylic acid tert-butyl ester (XXIIa)

A solution of the tertiary alcohol from above (2.786 g) in 30 mL of methylene chloride is cooled to −5° C. At this temperature is added triethylamine (4.33 g) followed by dropwise addition of a solution of methanesulphonyl chloride (2.45 g) in 7 mL of methylene chloride within 20 minutes. The reaction mixture is stirred for 60 minutes at −5° C. and quenched with 20 mL of pH 3.0 buffer solution, 30 mL of 10% aqueous citric acid and 50 mL of saturated aqueous sodium bicarbonate solution. The organic phase is separated and washed twice with 100 mL of water. The combined aqueous washings are re-extracted with 100 mL of methylene chloride and the organic phases combined. Removal of the solvent in vacuum produced 3.41 g of the crude product as an oil. Chromatography on silica-gel, eluting with a toluene/ethyl acetate mixture (9/1) gave 2.26 g of the pure desired product.

$^1$HNMR (CDCl$_3$) 6.85-6.65(3H, m, Ph), 5.10-4.88(2H, m, CH$_2$=C CHOBoc), 4.64(1H, m, CHNHBoc), 4.11(2H, t, CH$_2$O), 3.83(3H, s, MeO), 3.58(2H, t, CH$_2$O), 3.35(3H, s, MeO), 3.2(1H, t, CH), 2.60-2.30(2H, m PhCH$_2$), 2.10(2H, m), 1.80(3H, s, Me), 1.79-1.60(3H, m), 1.52(9H, s, tBu), 1.48(9H, s, tBu), 0.81(6H, m, 2×iPr).

I) (2S,3S)-3-tert-Butoxycarbonyloxy-5-isopropylidene-2-{(S)-2-[4-methoxy-3-(3-methoxy-propoxy)-benzyl]-3-methyl-butyl}-6-oxo-piperidine-1-carboxylic acid tert-butyl ester (XXIIIa)

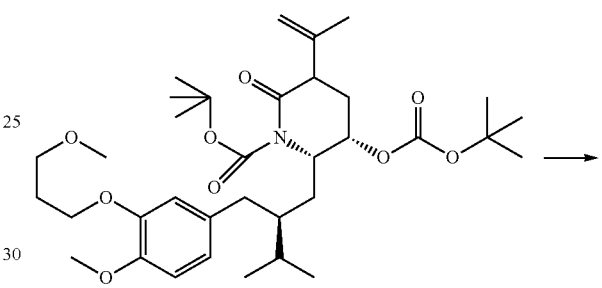

(2S,3S)-3-tert-Butoxycarbonyloxy-5-isopropenyl-2-{(S)-2-[4-methoxy-3-(3-methoxy-propoxy)-benzyl]-3-methyl-butyl}-6-oxo-piperidine-1-carboxylic acid tert-butyl ester (XXIIa)

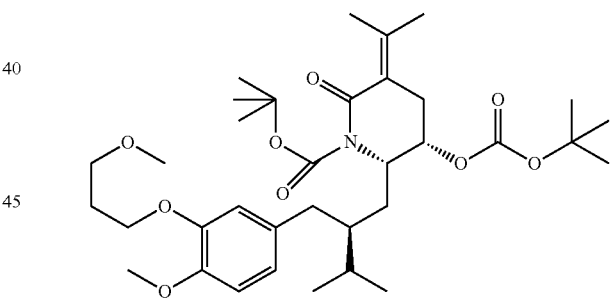

(2S,3S)-3-tert-Butoxycarbonyloxy-5-isopropylidene-2-{(S)-2-[4-methoxy-3-(3-methoxy-propoxy)-benzyl]-3-methyl-butyl}-6-oxo-piperidine-1-carboxylic acid tert-butyl ester (XXIIIa)

A solution of the compound with the exocyclic double bond (1.95 g) in 25 mL of ethyl acetate is treated with 1 g of active charcoal and 0.3 g of triethylamine. The mixture was stirred for 2 hours at room temperature and filtered. The solid is washed with 10 mL of ethyl acetate and the solvent is removed in vacuum to produce 1.90 g of a semi-solid. This was crystallised from hexane to give 1.257 g of pure product.

$^1$HNMR (CDCl$_3$) 6.80-6.65(3H, m, Ph), 4.95(2H, m, CHOBoc), 4.75(1H, m, CHNHBoc), 4.10(2H, t, CH$_2$O), 3.83(3H, s, MeO), 3.58(2H, t, CH$_2$O), 3.35(3H, s, MeO), 2.85-2.55(2H, m PhCH$_2$), 2.45-2.30(2H, m), 2.10(5H, m), 1.73-1.40(23H, m), 0.81(3H, d, iPr), 0.71(3H, d, iPr).

J) (2S,3S,5S)-3-tert-Butoxycarbonyloxy-5-isopropyl-2-{(S)-2-[4-methoxy-3-(3-methoxy-propoxy)-benzyl]-3-methyl-butyl}-6-oxo-piperidine-1-carboxylic acid tert-butyl ester (XXIVa)

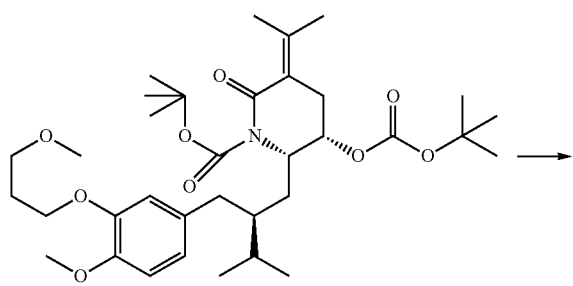

(2S,3S)-3-tert-Butoxycarbonyloxy-5-isopropylidene-2-{(S)-2-[4-methoxy-3-(3-methoxy-propoxy)-benzyl]-3-methyl-butyl}-6-oxo-piperidine-1-carboxylic acid tert-butyl ester
(XXIIIa)

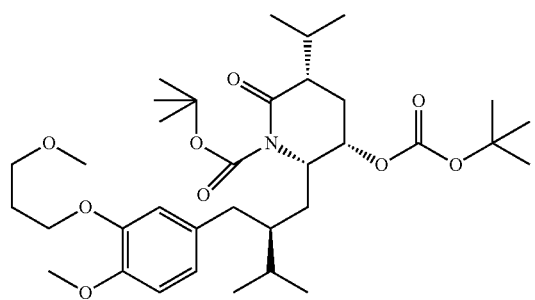

(2S,3S,5S)-3-tert-Butoxycarbonyloxy-5-isopropyl-2-{(S)-2-[4-methoxy-3-(3-methoxy-propoxy)-benzyl]-3-methyl-butyl}-6-oxo-piperidine-1-carboxylic acid tert-butyl ester
(XXIVa)

A solution of the olefin from above (0.38 g) in 10 mL of ethyl acetate is treated with 0.3 g of Pt/C-5%. Triethylamine (0.086 g) is added and the suspension placed under an atmosphere of hydrogen. The temperature is increased to 50° C. and the pressure to 5 bar. The reaction mixture is stirred under these conditions for 24 hours, cooled to room temperature and the catalyst removed by filtration. The solvent is removed in vacuum and the residue purified by chromatography over silica-gel, eluting with toluene/ethyl acetate/3:1). The product containing fractions are combined and the solvent removed to give the desired compound (0.3 g) as an oil.

$^1$HNMR (CDCl$_3$) 6.85-6.70(3H, m, Ph), 5.00(1H, m, CHOBoc), 4.65(1H, m, CHNHBoc), 4.15(2H, t, CH$_2$O), 3.83 (3H, s, MeO), 3.58(2H, t, CH$_2$O), 3.35(3H, s, MeO), 2.60-2.40(2H, m PhCH$_2$), 2.10(2H, m, CH$_2$), 2.00-1.65(4H, m), 1.58-1.30(20H, m), 0.85(6H, m, 2×Me), 0.75(6H, m, 2×Me).

K) {(1S,3S)-1-((2S,4S)-4-Isopropyl-5-oxo-tetrahydro-furan-2-yl)-3-[4-methoxy-3-(3-methoxy-propoxy)-benzyl]-4-methyl-pentyl}-carbamic acid tert-butyl ester (XIa)

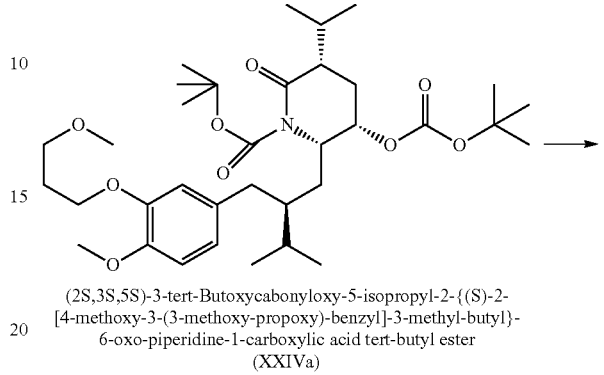

(2S,3S,5S)-3-tert-Butoxycabonyloxy-5-isopropyl-2-{(S)-2-[4-methoxy-3-(3-methoxy-propoxy)-benzyl]-3-methyl-butyl}-6-oxo-piperidine-1-carboxylic acid tert-butyl ester
(XXIVa)

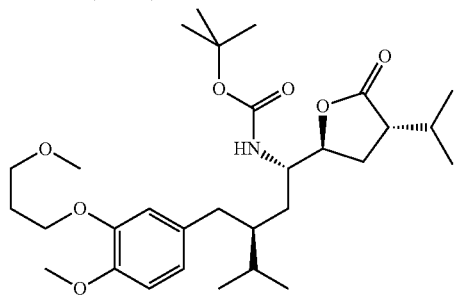

{(1S,3S)-1-((2S,4S)-4-Isopropyl-5-oxo-tetrahydro-furan-2-yl)-3-[4-methoxy-3-(3-methoxy-propoxy)-benzyl]-4-methyl-pentyl}-carbamic acid tert-butyl ester
(XIa)

via

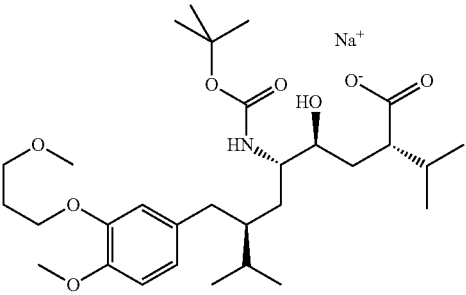

Sodium; (2S,4S,5S,7S)-5-tert-butoxy carbonylamino-4-hydroxy-2-isopropyl-7-[4-methoxy-3-(3-methoxy-propoxy)-benzyl]-8-methyl-nonanoate
(XXVa)

A solution of the piperidinone (0.28 g) in 3 mL of tetrahydrofuran is treated, at room temperature, with 1 mL of a 2.0M solution of sodium hydroxide in water. Benzyltriethylammonium chloride (2 mg) is added and the mixture stirred at 40° C. for 5 hours. Ethanol (1 mL) is added and stirring continued at 40° C. for 24 hours. The mixture is then cooled to room temperature and glacial acetic acid (2 mL) is added. The acid mixture is extracted into a toluene/water mixture and the organic phase separated. The solvent is removed in vacuum to give an oil. This oil is re-dissolved in 5 mL of glacial acetic acid and stirred for 24 hours at 100° C. The acetic acid is then removed in vacuum and the residue purified by preparative thin layer chromatography, eluting with ethyl acetate/hexane, 1/1. This provided 0,0476 g of the desired product.

$^1$HNMR (CDCl$_3$) 6.81-6.70(3H, m, Ph), 4.40(1H, m, CHO-Lactone ring), 4.10(2H, t, CH$_2$O), 3.85-3.79(4H, m, MeO+CHNBoc), 3.58(2H, t, CH$_2$O), 3.35(3H, s, MeO), 2.85-2.55(2H, m PhCH$_2$), 2.65(1H, dd, PhCH), 2.55(1H, m, CHCO-lactone), 2.40(1H, dd, PhCH), 2.12-2.05(5H, m), 1.70-1.30(13H, m), 1.05(3H, d, Me), 0.95(3H, d, Me), 0.85 (6H, d, iPr).

$[\alpha]_D$=−6.1° (c=3 in CH$_2$Cl$_2$).

Examples for the Preparation of Compound (VIIIb)

Preparation of 2-(R)-(4-Nosyloxy)-isovalerianic acid methylester (R$_4$=i-propyl, R$_9$=methyl)

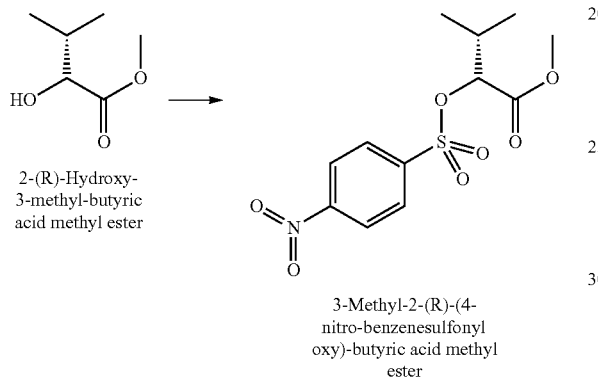

2-(R)-Hydroxy-3-methyl-butyric acid methyl ester

3-Methyl-2-(R)-(4-nitro-benzenesulfonyl oxy)-butyric acid methyl ester 43.6 g (330 mmol) 2-(R)-hydroxy-isovalerianic acid methylester, which can be prepared according to a literature procedure (Lit.: 1a-1c) are dissolved in 50 ml of dichloromethane. To the solution is added 38.4 g (379.4 mmol) of triethylamine and 4.0 g (33 mmol) of dime-thylamino pyridine. After cooling to 0° C. a solution of 80.42 (362.9 mmol) 4-nitrobenzene-sulfonylchloride in 250 ml di-chloromethane is added slowly under stirring during 45 minutes. After stirring over night the reaction mixture is cooled to 0° C. and 25 ml 2N hydrochloric acid is added to adjust the pH to 3.5. The aqueous phase is extracted with 2×10 ml of dichloromethane and the combined organic phase is washed with 100 ml of water. The organic phase is evaporated in vacuum. The resulting orange oil is re-dissolved in 200 ml of toluene and extracted with 30 ml 1N hydrochloric acid, 50 ml of brine, 50 ml of saturated sodium bicarbonate solution and again with brine. The organic phase is then filtered via a pad of silica gel and the product is eluted with around 2 liters of toluene. The collected product fractions are evaporated in vacuum to give an orange oil (91.5 g) which crystallizes after seeding and cooling in the refrigerator. The resulting crystals are triturated with pentane and are filtered and washed with 2×50 ml of pentane to give after drying 84.3 g of crystalline product. m.p.: 46-48° C.; $[\alpha]_D$=+6.5° (1% CHCl$_3$)

$^1$H-NMR (CDCl$_3$): 8.34 (2H, d), 8.08 (2H. d), 4.77 (1H, d), 3.61 (3H, s), 2.17-2.24(1H, m), 0.91 (3H, d), 0.86 (3H, d).

Literature: 1a) Tetrahedron, 46, 6623 (1990)

1b) J. Chem. Soc.; Perk. Trans. 1, (12), 1427 (1996)

1c) J. Org. Chem., 52, 4978 (1987)

Preparation of [R)-2-Isopropyl-3-methoxycarbonyl-succinic acid dimethyl ester (R$_4$=i-propyl, all R$_9$=methyl)

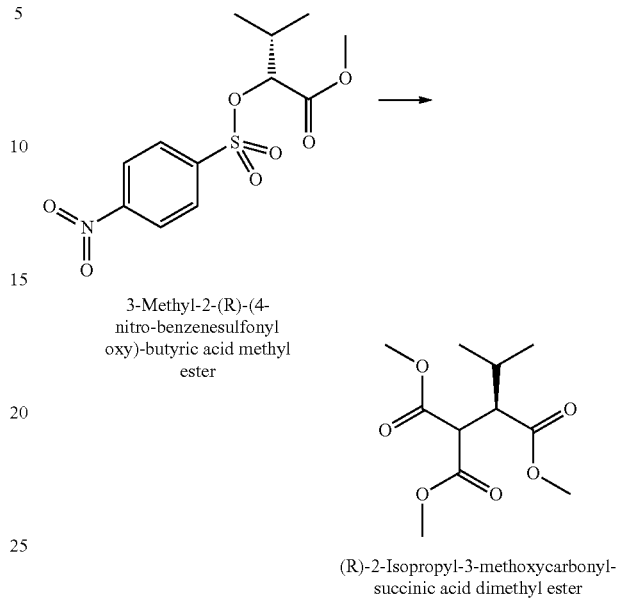

3-Methyl-2-(R)-(4-nitro-benzenesulfonyl oxy)-butyric acid methyl ester (R)-2-Isopropyl-3-methoxycarbonyl-succinic acid dimethyl ester A 500 ml three necked flask is charged with 16.8 g of sodium hydride (60% in mineral oil), 420 mmol. The NaH is washed 3 times with 20 ml portions of hexane under a flow of argon gas. Then 150 ml of n-dipropyl ether is added. The reaction mixture is cooled to 0° C. and 59.45 g (450 mmol) of dimethyl malonate, dissolved in 50 ml of n-dipropyl ether is slowly added under stirring. Strong hydrogen evolution and a temperature increase is observed. Temperature is kept at 15° C. during addition. A white, thick suspension is formed. Additional 50 ml of n-dipropyl ether is added to delute the heterogenous mixture. The reaction temperature is increased to 50° C. for 2 hours to complete the deprotonation. At this temperature a solution of the "nosylate", 47.58 g (150 mmol) in 120 ml n-dipropyl ether is added to the heterogenous mixture. The very thick brown suspension is heated at an internal temperature of 85° C. for 24 hours. After that time complete conversion of the nosylate is observed (GC). The reaction mixture is cooled to room temperature and quenched by careful addition to a mixture of 150 ml toluene and 150 ml water. The aqueous phase is extracted two times with 50 ml of toluene. The organic phases are combined and washed with 2×50 ml sodium bicarbonate, 2×50 ml 2N hydrochloric acid, and finally with 3×50 ml water to give after evaporation of the solvents in vacuum 48.2 g of a yellow oil. This oil is triturated with 150 ml hexane under stirring to give after evaporation 28 g of a slightly yellow oil. This oil is filtered through a pad of silica gel with a mixture of toluene/ethyl acetate (9:1). Chromatography fractions which contain pure product are combined and the solvent is evaporated in vacuum to give an almost colourless oil which crystallises in the refrigerator over night. The crystals are triturated with cold pentane, filtered and washed with small amounts of pentane to give after drying in vacuum 9.5 g of almost white product.

mp.: 45-48° X, $[\alpha]_D$=+62.5° (1% in MeOH)

$^1$H-NMR (CDCl$_3$): 3.87 (1H, d), 3.74 (3H, s), 3.70 (3H, s), 3.68 (3H, s), 3.12 (1H, dd), 1.78-1.85 (1H, m), 1.01 (3H, d), 0.88 (3H, d).

What is claimed is:

1. A compound of the formula

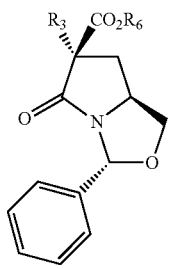

(IIc)

wherein $R_3$ is branched $C_{3-6}$alkyl, and $R_6$ is $C_{1-20}$alkyl, $C_{3-12}$cycloalkyl, $C_{3-12}$cycloalkyl-$C_{1-6}$alkyl, $C_{6-10}$aryl or $C_{6-10}$aryl-$C_{1-6}$alkyl; and wherein the phenyl ring shown in the structure may be substituted by one or more residues selected from the group consisting of $C_1$-$C_7$-alkyl, hydroxy, $C_1$-$C_7$-alkoxy, $C_2$-$C_8$-alkanoyl-oxy, halogen, nitro, cyano, and $CF_3$.

2. A compound of the formula

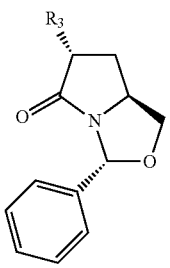

(IId)

wherein $R_3$ is branched $C_{3-6\ alkyl}$.

3. The compound of claim 1 wherein $R_6$ is $C_{1-4}$ alkyl.

4. The compound of claim 1 wherein $R_6$ is methyl or ethyl.

5. The compound of claim 1 wherein the phenyl ring is substituted with two or three residues selected from the group consisting of $C_1$-$C_7$-alkyl, hydroxy, $C_1$-$C_7$-alkoxy, $C_2$-$C_8$-alkanoyl-oxy, halogen, nitro, cyano, and $CF_3$.

6. The compound of claim 2 wherein $R_3$ is i-propyl.

* * * * *